(12) United States Patent
Jimenez et al.

(10) Patent No.: US 8,664,219 B2
(45) Date of Patent: *Mar. 4, 2014

(54) AMINOPYRIMIDINES USEFUL AS INHIBITORS OF PROTEIN KINASES

(75) Inventors: Juan-Miguel Jimenez, Abingdon (GB); Andrew Miller, Upton (GB); Jeremy Green, Waltham, MA (US); Huai Gao, Arlington, MA (US); Gregory Henkel, Carlsbad, CA (US); Michael Liu, Oceanside, CA (US); Timothy Neuberger, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 516 days.

This patent is subject to a terminal disclaimer.

(21) Appl. No.: 12/791,976

(22) Filed: Jun. 2, 2010

(65) Prior Publication Data

US 2011/0020376 A1   Jan. 27, 2011

Related U.S. Application Data

(63) Continuation of application No. PCT/US2008/056423, filed on Mar. 10, 2008.

(60) Provisional application No. 60/906,086, filed on Mar. 9, 2007, provisional application No. 60/953,020, filed on Jul. 31, 2007.

(51) Int. Cl.
*C07D 403/12* (2006.01)
*A61K 31/506* (2006.01)

(52) U.S. Cl.
USPC .............. 514/235.8; 514/252.19; 514/256; 544/122; 544/295; 544/328

(58) Field of Classification Search
USPC .......... 544/122, 295, 328; 514/235.8, 252.19, 514/256
See application file for complete search history.

(56) References Cited

U.S. PATENT DOCUMENTS

| | | |
|---|---|---|
| 3,133,081 A | 5/1964 | Lafferty et al. |
| 3,755,322 A | 8/1973 | Winter et al. |
| 3,935,183 A | 1/1976 | Baron et al. |
| 3,998,951 A | 12/1976 | Harnish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 6,558,657 B1 | 5/2003 | Mandeville, III et al. |
| 6,562,971 B2 | 5/2003 | Frauenkron et al. |
| 6,569,499 B2 | 5/2003 | Grammatica et al. |
| 6,579,983 B1 | 6/2003 | Batchelor et al. |
| 6,589,958 B1 | 7/2003 | Frietze |
| 6,593,326 B1 | 7/2003 | Bradbury et al. |
| 6,610,677 B2 | 8/2003 | Davies et al. |
| 6,613,776 B2 | 9/2003 | Knegtel et al. |
| 6,638,926 B2 * | 10/2003 | Davies et al. ............ 514/217.05 |
| 6,641,579 B1 | 11/2003 | Bernardi et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,716,851 B2 | 4/2004 | Cai et al. |
| 6,727,251 B2 | 4/2004 | Bebbington et al. |
| 6,743,791 B2 | 6/2004 | Cao et al. |
| 6,825,190 B2 | 11/2004 | Moon et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,884,804 B2 | 4/2005 | Choon-Moon |
| 6,919,338 B2 | 7/2005 | Mortlock et al. |
| 6,949,544 B2 | 9/2005 | Bethiel et al. |

(Continued)

FOREIGN PATENT DOCUMENTS

| | | |
|---|---|---|
| DE | 2458965 | 6/1976 |
| EP | 0019811 | 12/1980 |

(Continued)

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Hardt et al., Glycogen Synthase Kinase—3beta: A Novel Regulator of Cardiac Hypertrophy and Development, Circulation Research, 90:1055-1063, 2002.*
Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).
Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).
Tanji, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).
Charpiot, B. et al., "Quinazolines: Combined type 3 and 4 phosphodiesterase inhibitors", Bioorg. Med. Chem. Lett., 8 (20), 2891-2896 (1998).

(Continued)

*Primary Examiner* — Deepak Rao
(74) *Attorney, Agent, or Firm* — Rory C. Stewart

(57) ABSTRACT

The present invention relates to compounds useful as inhibitors of protein kinases. The invention also provides pharmaceutically acceptable compositions comprising those compounds and methods of using the compounds and compositions in the treatment of various disease, conditions, and disorders. The invention also provides processes for preparing compounds of the invention.

22 Claims, No Drawings

(56) References Cited

U.S. PATENT DOCUMENTS

| | | |
|---|---|---|
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,739 B2 | 10/2006 | Bebbington et al. |
| 7,179,826 B2 | 2/2007 | Bebbington et al. |
| 7,253,187 B2 | 8/2007 | Cao et al. |
| 7,304,061 B2 | 12/2007 | Hale et al. |
| 7,345,054 B2 | 3/2008 | Hale et al. |
| 7,361,665 B2 | 4/2008 | Ledeboer et al. |
| 7,390,815 B2 | 6/2008 | Davies et al. |
| 7,427,681 B2 | 9/2008 | Bebbington et al. |
| 7,473,691 B2 | 1/2009 | Davies et al. |
| 7,491,730 B2 | 2/2009 | Forster et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,579,349 B2 | 8/2009 | Nowak et al. |
| 7,625,913 B2 | 12/2009 | Bebbington et al. |
| 7,691,853 B2 | 4/2010 | Bebbington et al. |
| 7,737,151 B2 | 6/2010 | Mortimore et al. |
| 7,767,672 B2 | 8/2010 | Binch et al. |
| 7,820,685 B2 | 10/2010 | Binch et al. |
| 7,863,282 B2 | 1/2011 | Bebbington et al. |
| 7,872,129 B2 | 1/2011 | Forster et al. |
| 7,951,820 B2 | 5/2011 | Bebbington et al. |
| 7,982,037 B2 | 7/2011 | Bebbington et al. |
| 7,989,456 B2 | 8/2011 | Mortimore et al. |
| 8,242,272 B2 * | 8/2012 | Jimenez et al. ............ 544/328 |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055044 A1 | 3/2003 | Davies et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0069239 A1 | 4/2003 | Cai et al. |
| 2003/0069248 A1 | 4/2003 | Chakravarty et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington et al. |
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0049032 A1 | 3/2004 | Charrier et al. |
| 2004/0097501 A1 | 5/2004 | Bebbington et al. |
| 2004/0097531 A1 | 5/2004 | Ledeboer et al. |
| 2004/0157893 A1 | 8/2004 | Bebbington et al. |
| 2004/0167141 A1 | 8/2004 | Bebbington et al. |
| 2004/0214814 A1 | 10/2004 | Bebbington et al. |
| 2004/0229875 A1 | 11/2004 | Cao et al. |
| 2005/0004110 A1 | 1/2005 | Bebbington et al. |
| 2005/0038023 A1 | 2/2005 | Bebbington et al. |
| 2005/0049246 A1 | 3/2005 | Bemis et al. |
| 2005/0228005 A1 | 10/2005 | Moon et al. |
| 2005/0234059 A1 | 10/2005 | Hale et al. |
| 2006/0270660 A1 | 11/2006 | Charrier et al. |
| 2007/0179125 A1 | 8/2007 | Fraysse et al. |
| 2007/0190634 A1 | 8/2007 | Bebbington et al. |
| 2007/0265263 A1 | 11/2007 | Cao et al. |
| 2008/0287444 A1 | 11/2008 | Bebbington et al. |
| 2009/0181938 A1 | 7/2009 | Binch et al. |
| 2009/0221602 A1 | 9/2009 | Charrier et al. |
| 2010/0022502 A1 | 1/2010 | Jimenez et al. |
| 2010/0022507 A1 | 1/2010 | Jimenez et al. |
| 2010/0137305 A1 | 6/2010 | Binch et al. |
| 2010/0215772 A1 | 8/2010 | Mortimore et al. |
| 2010/0267768 A1 | 10/2010 | DeMattei et al. |
| 2010/0310675 A1 | 12/2010 | Binch et al. |
| 2010/0317641 A1 | 12/2010 | Mortimore et al. |
| 2011/0020376 A1 | 1/2011 | Jimenez et al. |
| 2011/0020377 A1 | 1/2011 | Pierce et al. |
| 2011/0020469 A1 | 1/2011 | Binch et al. |
| 2011/0021559 A1 | 1/2011 | Jimenez et al. |
| 2011/0046104 A1 | 2/2011 | Mortimore et al. |
| 2011/0060013 A1 | 3/2011 | Mortimore et al. |
| 2011/0086856 A1 | 4/2011 | Bebbington et al. |
| 2011/0269732 A1 | 11/2011 | Golec et al. |

FOREIGN PATENT DOCUMENTS

| | | |
|---|---|---|
| EP | 136976 | 4/1985 |
| EP | 0302312 | 2/1989 |
| GB | 2052487 | 1/1981 |
| JP | 10-130150 | 5/1998 |
| JP | 2000-026421 | 1/2000 |
| JP | 06-65237 | 10/2007 |
| WO | 9208715 | 5/1992 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0039101 | 6/2000 |
| WO | 0038675 | 7/2000 |
| WO | 0042029 | 7/2000 |
| WO | 0059509 | 10/2000 |
| WO | 0078757 | 12/2000 |
| WO | 0112621 | 2/2001 |
| WO | 0139777 | 6/2001 |
| WO | 0140215 | 6/2001 |
| WO | 0144242 | 6/2001 |
| WO | 0147879 | 7/2001 |
| WO | 0147897 | 7/2001 |
| WO | 0160816 | 8/2001 |
| WO | 0164655 | 9/2001 |
| WO | 0179198 | 10/2001 |
| WO | 0174768 | 11/2001 |
| WO | 0125220 | 12/2001 |
| WO | 0208244 | 1/2002 |
| WO | 0218346 | 3/2002 |
| WO | 0222601 | 3/2002 |
| WO | 0222602 | 3/2002 |
| WO | 0222603 | 3/2002 |
| WO | 0224667 | 3/2002 |
| WO | 0247690 | 6/2002 |
| WO | 0250065 | 6/2002 |
| WO | 0250066 | 6/2002 |
| WO | 02057259 | 7/2002 |
| WO | 02059111 | 8/2002 |

(56) References Cited

FOREIGN PATENT DOCUMENTS

| WO | 02059112 | 8/2002 |
| --- | --- | --- |
| WO | 02062789 | 8/2002 |
| WO | 02066461 | 8/2002 |
| WO | 02068415 | 9/2002 |
| WO | 02079197 | 10/2002 |
| WO | 03026664 | 4/2003 |
| WO | 03077921 | 9/2003 |
| WO | 03078426 | 9/2003 |
| WO | 03078427 | 9/2003 |
| WO | 04000833 | 12/2003 |
| WO | 2004013140 | 2/2004 |
| WO | 2004037814 | 5/2004 |
| WO | 2007023382 | 1/2007 |
| WO | 2007041358 | 4/2007 |
| WO | 2007/056221 | 5/2007 |
| WO | 2007056163 A | 5/2007 |
| WO | 2007056164 A1 | 5/2007 |
| WO | 2007059299 | 5/2007 |
| WO | 2008057940 | 5/2008 |
| WO | WO2008077086 | 6/2008 |

OTHER PUBLICATIONS

Shikhaliev, K.S. et al., "Heterocyclization of quinazol-2-ylguanidines. 1. Reaction with amino acids", Chem. Heterocycl. Compd., 35 (7), 818-820 (1999).
Singh, S.P. et al., "Synthesis & Mass Spectra of Some Substituted 2-(2'-Benzazolylamino)pyrimidines", Indian J. Chem. Sect. B, 22(1); 37-42 (1983).
Ti, J. et al., "Anticandidal activity of pyrimidine-peptide conjugates", J. Med. Chem., 23(8), 913-918 (1980).
Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).
Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).
Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).
Myers, M.R. et al., "The synthesis and SAR of new 4-(N-alkyl-N-phenyl)amino-6,7-dimethoxyquinazolines and 4-(N-alkyl-N-phenyl)aminopyrazolo[3,4-d]pyrimidines, inhibitors of CSF-1R tyrosine kinase activity", Bioorg. Med. Chem. Lett, 7, 4, 421-424 (1997).
Agarwal, N. et al., "Suitably functionalised pyrimidines as potential antimycotic agents", Bioorg. Med. Chem. Lett., 10, 8, 703-706 (2000).
Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).
Noell, C.W. et al., "Potential Purine Antagonists. XX. The Preparation and Reactions of Some Methylthiopurines", J. Am. Chem. Soc., 81(22), 5997-6007 (1959).
Lubbers, T. et al., "Design, synthesis, and structure—activity relationship studies of ATP analogues as DNA gyrase inhibitors", Bioorg. Med. Chem. Lett., 10, 8, 821-826 (2000).
D'Atri, G. et al., "Novel pyrimidine and 1,3,5-triazine hypolipemic agents", J. Med. Chem. 27(12), 1621-1629 (1984).
Venugopalan, B. et al., "Synthesis and antimalarial activity of pyrido[3,2-f]quinozalines and their oxides", Indian J. Chem. Sect. B, 34, 9, 778-790 (1995).
Curd, F.H.S. et al, "Synthetic antimalarials. Part XVII. Some aminoalkylaminoquinoline derivatives", J. Chem. Soc., 899-909 (1947).
Haworth, R.D. et al., "Synthetic antimalarials. Part XXVII. Some derivatives of phthalazine, quinoxaline, and isoquinoline", J. Chem. Soc., 777-782 (1948).
Nair, M.D., et al., "3-Chloroisocarbostyril & Its Chlorination Products", Indian J. Chem., 467-470 (1967).
Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).
Gnecco, D. et al., "An Improved Preparation of 1-Methyl-4-Cyano-4-phenylpiperidine", Org. Prep. Proced. Int., 18 (4), 478-480 (1996).
Fedorynski, M. et al., "Synthesis of 1-Arycyclopropanecarbonitriles under Phase-transfer Catalytic Conditions", Org. Prep. Proced. Int., 27(3), 355-359 (1995).
Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).
Prasad, G. et al., "18-Crown-6 as a catalyst in the dialkylation of o-nitrophenacyl derivatives", J. Org. Chem., 25, 7188-7190 (1991).
Moss, R.A. et al., "Conversion of 'Obstinate' Nitriles to Amidines by Garigipati's Reaction", Tetrahedron Lett., 36(48), 8761-8764 (1995).
Garigipati, R.S., "An efficient conversion of nitriles to amidines", Tetrahedron Lett., 31(14), 1969-1972 (1990).
Warner, S.L. et al, "Targeting Aurora-2 Kinase in Cancer," Mol. Cancer Thera., 2, 589-585, 2003.
Wagman, A.S. et all, "Discovery and Development of GSK3 Inhibitors for the Treatment of Type 2 Diabetes," Current Pharmaceutical Design, 10, 1105-1137 (2004).
Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).
Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).
Soriano, P. et al., "Targeted Disruption of the C-SIC Pmto-Oncogene Leads to Osteopetrosis in Mice," Cell, 64: 693-702, (1991).
Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).
Casanova, B. et al., "Revisión crítica de la patogenia actual de la esclerosis múltiple y futuras direcciones posibles," Rev. Neurol., 28 (9): 909-915 (1999).
Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Simone, J.V., "Oncology: Introduction" in Cecil Textbook in Medicine, 20th ed., vol. 1, 1004-1010 (1996).
Coleman, R.A., "The Biological Evaluation of New Compounds" in Medicinal Chemistry: Principles and Practice, King, Frank D. ed, Royal Society of Chemistry, 53-66 (1994).
The Condensed Chemical Dictionary, Sixth Edition by Arthur and Elizabeth Rose, 38 (1961).
Damasio, A.R., "Alzheimer's Disease and Related Dementia," in Cecil Textbook of Medicine, 20th ed., 2: 1992-1996 (1996).
Rogers, E. et al., "The aurora kinase AIR-2 functions in the release of chromosome cohesion in *Caenorhabditis elegans* meiosis," J. Cell Biol., 157(2): 219-229 (2002).
Fisher A., "Therapeutic Strategies in Alzheimer's Disease: M1 Muscarinic Agonists," Jpn. J. Pharmacol., 84(2):101-12 (2000).
Frame, M.C., "Src in cancer: deregulation and consequences for cell behaviour," Biochimica et Biophysica Acta., 1602, 114-130 (2002).
Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).
Ganellin, C.R., "Past Approaches to Discovering New Drugs as Medicines" in Medicinal Chemistry, Principles and Practices. King, Frank D. ed, Royal Society of Chemistry, 189-205 (1994).
Hamdane, M. et al., "A Therapeutic Target in Alzheimer Neurodegeneration," J. Mol. Neurosci., 19(3): 275-87 (2002).
Hardt, S.E. et al., "Glycogen Synthase Kinase-3β—A Novel Regulator of Cardiac Hypertrophy and Development," Circulation Research, 90: 1055-1063 (2002).

(56) References Cited

OTHER PUBLICATIONS

Parnell, E.W., "2-Cyano-4-nitrophenylhydrazine and 3-Amino-5-nitroindazole", J. Chem. Soc., 2363-2365 (1959).
Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).
Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).
Okafor, C.O., "Studies in the Heterocyclic Series. X. 1,3,9-Triazaphenothiazine Ring System, a New Phenothiazine Ring," J. Org. Chem., 40(19): 2753-2755 (1975).
Jambhekar, S.S., "Biopharmaceutical Properties of Drug Substances" in Principles of Medicinal Chemistry, 4th ed., 12-24, (1995).
Layzer, R.B., "Section Five—Degenerative Diseases of the Nervous System" in Cecil Textbook of Medicine, 20th ed., 2: 2050-2057 (1996).
Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med . Chem., 38 (18): 3547-3557 (1995).
Medwid, J.B. et al., "Preparation of Triazolo[ 1,5-c]pyrimidines as Potential Antiasthma Agents," J. Med. Chem. 33, 1230-1241 (1990).
Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).
Cohen, P., "Dissection of the Protein Phosphorylation Cascades Involved in Insulin and Growth Factor Action", Biochem. Soc. Trans., 21, 555-567 (1993).
Haq, S. et al., "Glycogen Synthase Kinase-3β Is a Negative Regulator of Cardiomyocyte Hypertrophy", J. Cell Biol., 151(1), 117-129 (2000).
Fischer, P.M. et al., "Inhibitors of Cyclin-Dependent Kinases as Anti-Cancer Therapeutics", Current Med. Chem., 7, 1213-1245 (2000).
Mani, S. et al., "Cyclin-dependent kinase: novel anticancer agents", Exp. Opin. Invest. Drugs., 8, 1849-1870 (2000).
Fry, D.W. et al., "Inhibitors of cyclin-dependent kinases as therapeutic agents for the treatment of cancer", Current Opin. Oncol. Endoc. & Metab. Investig., 2-40-59 (2000).
Bokemeyer, D. et al., "Multiple intracellular MAP kinase signaling cascades", Kidney Int., 49, 1187-1198 (1996).
Anderson, N.G. et al., "Multiple intracellular MAP kinase signaling cascades", Nature, 343, 651-653 (1990).
Crews, C.M. et al., "The Primary Structure of MEK, a Protein Kinase That Phosphorylates the ERK Gene Product", Science, 258, 478-480 (1992).
Bjorbaek, C. et al, "Divergent Functional Roles for p90rsk Kinase Domains", J. Biol. Chem., 270(32), 18848-18552 (1995).
Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).
Raingeaud, J. et al., MMK3- and MMK6-Regulated Gene Expression Is Mediated by p38 Mitogen-Activated Protein Kinase Signal Transduction Pathway, Mol. Cell. Biol., 16, 1247-1255 (1996).
Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).
Moodie, S.A. et al., "Complexes of Ras-GTP with Raf-1 and Mitogen-Activated Protein Kinase Kinase", Science, 260 (5114), 1658-1661 (1993).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).
Sivaraman, V.S., et al., "Hyperexpression of Mitogen-activated Protein Kinase in Human Breast Cancer", J. Clin. Invest., 99(7), 1478-1483 (1997).

Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).
Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).
Kazuhiko, N. et al., "Akt/Protein Kinase B Prevents Injury-Induced Motoneuron Death and Accelerates Axonal Regeneration", J. of Neuroscience, 20(8), 2875-2986 (2000).
Molina, T.J. et al., "Profound block in thymocyte development in mice lacking p56lck", Nature, 357, 161-164 (1992).
Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).
Douglas, G. et al., "Introduction to viral diseases", Cecil Textbook of Medicine, 20th Edition, vol. 2, p. 1739-1747, (1996).
Salomon, S. et al., "Cancer Chemotherapy", Lange Medical Book, Basic and Clinical Pharmacology, 7th edition, 55, p. 881-884, (1997).
Torryiabe, K. et al., "Preparation of self-conaining arylthiazoles and insecticides", Chemical abstracts, [ Columbus, Ohio, 132:93314n, vol. 132, No. 8 (2000).
IUPAC Compendium of Chemical Terminology on a definition of "aliphatic compounds" found from http://www.chemsoc.org/chembytes/goldbook/index.htm (last visited on Nov. 18, 2007).
Caravajal et al., Aurora Kinases: New Targets for Cancer Therapy, Clin Cancer Res 2006:12(23), pp. 6869-6875, Dec. 1, 2006.
Johnson et al., Relationships between drug activity in NCI preclinical in vitro and in vivo models and early clinical trials, British Journal of Cancer (2001) 64(1 0): 1424-1431.
Gura, Systems for identifying New Drugs Are Often Faulty, Cancer Models, Science, vol. 278, No. 5340, pp. 1041-1042, Nov. 1997.
The International Search Report received in the corresponding PCT Application No. PCT/US2008/056423, (2008).
Alonso, M. et al., "GSK-3 Inhibitors: Discoveries and Developments", Current Medicinal Chemistry, 11, 755-763 (2004).
Anonymous, "Vertex Inhbitors of Aurora-2, glycogen synthase kinase-3 and Src Kinase", Expert Opin. Ther. Patents, 14(3): 439-443 (2004).
Baig, G.U. et al., "Triazines and Related Products. Part 28' Conversion of 3-Aryl-l-(2-cyanopheny1) triazenes into 3-Arylqu i nazol i n-4(3H)-ones with Formamide" J. Chem. Soc. Perkin Trans. I, 3765-2766 (1984).
Bischoff, J.R., et al., "A homologue of Drosophila aurora kinase is oncogenic and amplified in human colorectal cancers", The EMBO Journal, 17(11): 3052-3065 (1998).
Bischoff, J.R., et al., "The Aurora/Ipl1p kinase family: regulators of chromosome segregation and cytokinesis", Cell Biology, 9, 454-459 (1999).
Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).
Wolff, M.E., "Burger's Medicinal Chemistry and Drug Discovery," 5th ed., vol. 1: Principles and Practice, 975-977 (1995).
Cohen, P. et al., "The renaissance of GSK3," Nat. Rev. Mol. Biol., 2, 769-776 (2001).
Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).
Harrington, E.A. et al., "VX-680, a potent and selective small-molecule inhibitor of the Aurora kinases, suppresses tumor growth in vivo," Nat. Med., 10(3): 262-267 (2004).
Heutink, P., "Untangling tau-related dementia", Hum. Mol. Genet., 9(6): 979-986 (2000).
Nigg, E.A., "Mitotic Kinases as Regulators of Cell Division and its Checkpoints," Nat. Rev. Mol. Cell Biol., 2: 21-32 (2001).
Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).
Nakajima, Y. et al., "Pyrazoles agricultural and horticultural bactericides," CAPLUS listing Accession No. 1994:292136, JP 06065237 (1994).

(56) References Cited

OTHER PUBLICATIONS

Kelarev, V.I. et al., "Synthesis of amino derivatives of 1,3,5-triazine containing 1,3-4-thiadiazole fragments," Databaseca "Online!" Chemical Abstract Service, Columbus, OH, US; Database Accession No. 1998:69514 XP002242653 abstract & Izvestiya Vysshikh Uchebnkh Zavedenii, Khimiya I Khimicheskaya Tekhnologiya, 40(5): 27-32 (1997).
Chalmers, D.T. et al., "Corticotrophin-releasing factor receptors: from molecular biology to drug design," TiPS, 17, 769-776 (2001).
Kim, L. et al., "GSK3, a master switch regulating cell-fate specification and tumorigenesis," Current Opinion in Genetics & Development, 10:508-514 (2000).
Lyrer, P., Schweiz. Med. Woohen Schr., 124(45); 2005-2012 (1994).
Banker, G.S. et al., "Modern Pharmaceutics", 451 & 596, 3rd ed., Marcel Dekker, New York (1996).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Ivashchenko A. V. et al., "Synethsis and Study of Heteroaromatic Ligands Containing a Pyrimidine Ring", Khim. Geterotsikl. Soedin., (12), 1673-7, (1980) (in English).
Brownlees, J. et al., "Tau phosphorylation in transgenic mice expressing glycogen synthase kinase-3beta transgenes", Neuroreport., 8(15), 3251-5 (1997).
Biagi, G. et al., "Synthesis of 4,6 Disubstituted and 4,5,6-Trisubstituted-2-Phenyl-pyrimidines and Their Affinity Towards A1 Adenosine Receptors", Farmaco., 52(1), 61-65 (1997).
Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).
Zhang, Z. et al., "Destabilization of β catenin by mutations in presenilin-1 potentiates neuronal apoptosis", Nature, 395, 698-702 (1998).
Takashima, K. et al., "Tau Protein Kinase I is Essential for Amyloid β-Protein-Induced Neurotoxicity", PNAS 90, 7789-7793 (1993).
Pei, J. et al., "Distribution, Levels, and Activity of Glycogen Synthase Kinase-3 in the Alzheimer Disease Brain", J. Neuropathol. Exp., 56, 70-78 (1997).
Rueeger, H et al., "Design, synthesis and SAR of a series of 2-substituted 4-amino-quinazoline neuropeptide Y Y5 receptor antagonists", Bioorg. Med. Chem. Lett, 10(11), 1175-1180 (2000).
Glossary of Class Names of Organic Compounds and Reactive Intermediates Based on Structure found from http://www.chem.qmul.ac.uk/iupac/class/index.html (last visited on Nov. 18, 2007).
Nomenclature found from http://www.cem.msu.edu/~reusch/VirtualText/nomen1.htm (last visited on Nov. 18, 2007).
Coghlan, M.P. et al., "Selective small molecule inhibitors of glycogen synthase kinase-3 modulate glycogen metabolism and gene transcription", Chemistry & Biology, 7, 793-83 (2000).
Klein, P.S. et al., "A molecular mechanism for the effect of lithium on development", PNAS, 93: 8455-8459 (1996).
Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).
Massillon, D. et al., "Identification of the glycogenic compound 5-iodotubercidin as a general protein kinase inhibitor", Biochem J., 299: 123-128 (1994).
Fox T. et al., "A single amino acid substitution makes ERK2 susceptible to pyridinyl imidazole inhibitors of p38 MAP kinase", Protein Sci., 7: 2249-2255 (1998).
Takayanagi, H. et al., "Suppression of arthritic bone destruction by adenovirus-mediated csk gene transfer to synoviocytes and osteoclasts", J. Clin. Invest., 104, 137-146 (1999).
Boschelli et al., "Small molecule inhibitors of Src family kinases", Drugs of the Future, 25(7): 717-736 (2000).
Talamonti, M.S. et al., "Increase in activity and level of pp60c-src in progressive stages of human colorectal cancer", J Clin Invest., 91(1): 53-60 (1993).
Lutz M.L. et al., "Overexpression and Activation of the Tyrosine Kinase Src in Human Pancreatic Carcimona", Biochem. Biophys. Res. 243, 503-508 (1998).
Rosen, N. et al., "Analysis of pp60c-src Protein Kinase Activity in Human Tumor Cell Lines and Tissues", J.Biol. Chem., 261, 13754-13759 (1986).
Bolen, J.B. et al., "Activation of pp60c-src protein kinase activity in human colon carcinoma", PNAS, 84, 2251-2255 (1987).
Masaki, T. et al., "pp60c-src Activation in Hepatocellular Carcinoma of Humans and LEC Rats", Hapatology, 27, 1257 (1998).
Biscardi, J.S. et al., "c-Src, Receptor Tyrosine Kinases, and Human Cancer", Adv. Cancer Res., 76, 61 (1999).
Lynch, S.A. et al., "Increased Expression of the src Proto-Oncogene in Hairy Cell Leukemia and a Subgroup of B-Cell Lymphomas", Leukemia, 7(9), 1416-1422 (1993).
Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).
Staley, C.A. et al., "Decreased Tumorigenicity of a Human Colon Adenocarcinoma Cell Line by an Antisense Expression Vector Specific for c-Src", Cell Growth Diff., 8, 269-274 (1997).
Singhal, N. et al., "Synthesis and Antimalarial Activity of Some New Quinazoline Derivatives", Indian Chem. Soc., 61, 690-693 (1984).
Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).
Namikowa et al., "Akt/Protein Kinase B Prevents Injury-Induced Motoneuron Death and Accelerates Axonal Regeneration", The Journal of Neuroscience, Apr. 15, 2000, 20(8):2875-2886.

\* cited by examiner

AMINOPYRIMIDINES USEFUL AS INHIBITORS OF PROTEIN KINASES

CROSS-REFERENCE TO RELATED APPLICATIONS

This application is a continuation application of International Patent Application No. PCT/US2008/056423, filed on Mar. 10, 2008, which in turn claims the benefit under 35 U.S.C. 119, of U.S. Provisional Patent Application Nos. 60/906,086, filed on Mar. 9, 2007 and 60/953,020 filed on Jul. 31, 2007.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention.

BACKGROUND OF THE INVENTION

Glycogen synthase kinase-3 (GSK-3) is a serine/threonine protein kinase comprised of α and β isoforms that are each encoded by distinct genes [Coghlan et al., Chemistry & Biology 2000, 7, 793-803; and Kim and Kimmel, Curr. Opinion Genetics Dev., 2000 10, 508-514]. Protein kinases, particularly GSK-3, have been implicated in various diseases, disorders, and conditions including Diabetes, Alzheimer's, Huntington's, Amyotrophic Lateral Sclerosis, Parkinson's, Bipolar disorder, Schizophrenia, Cerebral stroke, Chemotherapeutic-dependent leukocytopenia and Cardiac Hypertrophy. [PCT Application Nos.: WO 99/65897 and WO 00/38675; Haq et al., J. Cell Biol. 2000, 151, 117-130; Hirotani et al, Circulation Research 101, 2007, pp. 1164-1174].

Inhibiting GSK-3 is the desired approach for treating these diseases, disorders, and conditions. In cardiac hypertrophy, active GSK-3 may be important for inhibiting hypertrophy. However, blocking GSK-3 appears to be important for protecting against apoptosis in hypertrophied cardiac myoctyes. [Haq et al., J. Cell Biol. 2000, 151, 117-130; Hirotani et al, Circulation Research 101, 2007, pp. 1164-1174].

GSK-3 regulates multiple downstream effectors associated with a variety of signaling pathways. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., PNAS 1996, 93, 8455-8459; Cross et al., Biochem. J. 1994, 303, 21-26); Cohen, Biochem. Soc. Trans. 1993, 21, 555-567; and Massillon et al., Biochem J. 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is associated with Alzheimer's disease. The hallmarks of this disease are the extracellular plaques formed by aggregated β-amyloid peptides and the formation of intracellular neurofibrillary tangles via the tau protein.

It has been shown that GSK-3 inhibition reduces amyloid-β peptides in an animal model of Alzheimer's disease. See pages 435, 438. Phiel et. al., Nature 423, 435-439 (2003). Mice over-expressing amyloid precursor protein (APP) treated with lithium (a GSK-3α inhibitor) over a three-week period showed over a 50% decrease in amyloid-β peptide tissue levels.

The neurofibrillary tangles contain hyperphosphorylated Tau protein, in which Tau is phosphorylated on abnormal sites. GSK-3 is known to phosphorylate these abnormal sites in cell and animal models. Conditional transgenic mice that over-express GSK-3 develop aspects of AD including tau hyperphosphorylation, neuronal apoptosis and spatial learning deficit. Turning off GSK-3 in these mice restores normal behavior, reduces Tau hyperphosphorylation and neuronal apoptosis. (Engel T et al., J Neuro Sci, 2006, 26, 5083-5090 and Lucas et al, EMBO J, 2001, 20, 27-39) Inhibitors of GSK-3 have also been shown to prevent hyperphosphorylation of Tau in cells [Lovestone et al., Current Biology 1994, 4, 1077-86; and Brownlees et al., Neuroreport 1997, 8, 3251-55].

GSK-3 as a target for psychosis and mood disorders, such as schizophrenia and bipolar disease, respectively, have been reported in the literature. AKT haplotype deficiency was identified in a subset of schizophrenic patients which correlated with increased GSK-3 activity. A single allele knockout of GSK-3β resulted in attenuated hyperactivity in response to amphetamine in a behavior model of mania.

Several antipsychotic drugs and mood stabilizers used to treat both schizophrenic and bipolar patients have been shown to inhibit GSK-3 (Emamian et al, Nat Genet, 2004, 36, 131-137; Obrien et al, J Neurosci, 2004, 24, 6791-6798; Beaulieu et al, PNAS, 2004, 101, 5099-5104; Li et al Int J Neuropsychopharmacol, 2006, pp 1-13; Gould T D, Expert Opin Ther Targets, 2006, 10, 377-392). Furthermore, a recent patent, US 2004/0039007 describes GSK-3 inhibitors that show anti-schizophrenic and anxiolytic effects in relevant mouse behavior models.

GSK-3 activity is associated with stroke. Wang et al. showed that IGF-1 (insulin growth factor-1), a known GSK-3 inhibitor, reduced infarct size in rat brains after transient middle cerebral artery occlusion (MCAO), a model for stroke in rats. [Wang et al., Brain Res 2000, 859, 381-5; Sasaki et al., Neurol Res 2001, 23, 588-92; Hashimoto et al., J. Biol. Chem 2002, 277, 32985-32991]. US 2004/0039007 describes the effect of GSK-3 inhibitors in MCAO, a stroke model in rats. These GSK-3 inhibitors significantly reduced striatal ischemic damage and reduced edema formation in rats. Additionally, the rats "demonstrated marked improvement in neurological function over the time course of the experiment."

For all the above reasons, there is a great need to develop compounds useful as inhibitors of protein kinases. In particular, it would be desirable to develop compounds that are useful as inhibitors of GSK-3, particularly given the inadequate treatments currently available for the majority of the disorders implicated in their activation.

SUMMARY OF THE INVENTION

This invention provides compounds and pharmaceutically acceptable compositions thereof that are useful as inhibitors of GSK-3 protein kinases.

These compounds are represented by formula I:

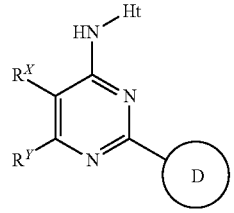

I or a pharmaceutically acceptable salt thereof, wherein the variables are as defined herein.

These compounds have surprising selectivity in blocking the tyrosine autophosphorylation form of the GSK-3 enzyme over the serine/threonine kinase form. These compounds are also surprisingly effective in increasing axonal and dendritic branching in neuronal cells, which is useful in the treatment of degenerative conditions such as stroke, Alzheimer's Disease, Parkinson's Disease, Huntington's Disease, Amyotrophic Lateral Sclerosis (ALS) Multiple Sclerosis (MS), Spinal Cord Injury, Traumatic Brain Injury, Charcot-Marie-Tooth, Leukocytopenia, Diabetes, Diabetic Neuropathy, and Osteoporosis.

These compounds are also effective as chemomodulators of repair, regeneration, and cellular differentiation.

The present invention also provides processes for preparing these compounds, compositions, pharmaceutical compositions, and methods of using such compounds and compositions for inhibiting protein kinases. These compounds are particularly useful as GSK-3 inhibitors.

These compounds and pharmaceutically acceptable compositions thereof are also useful for treating or preventing a variety of diseases, disorders or conditions, including, but not limited to, an autoimmune, inflammatory, proliferative, or hyperproliferative disease, a neurodegenerative disease, or an immunologically-mediated disease.

The compounds provided by this invention are useful for inhibiting kinases in vitro, in vivo, and ex vivo. These compounds also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention provides compounds of Formula I:

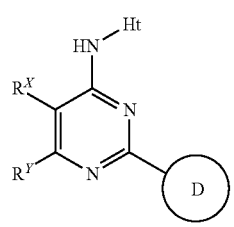

I or a pharmaceutically acceptable salt thereof, wherein:
Ht is

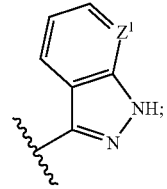

wherein any substitutable carbon on Ht is independently and optionally substituted with $—R^{10}$;

Ring D is a 3-10 membered cycloaliphatic or heterocyclyl; wherein said heterocyclyl contains 1-2 heteroatoms selected from O, N, or S; and wherein the cycloaliphatic or heterocyclyl is independently and optionally substituted with 1-5 $—R^5$; Ring D is bonded to the pyrimidine via a carbon atom;

$Z^1$ is N, CH, or $CR^{10}$;

$R^X$ is H, halo, or $C_{1-6}$alkyl, wherein the alkyl is independently and optionally substituted with 1-5 groups selected from halo, —CN, and —OR;

$R^Y$ is H, halo, $C_{1-6}$alkyl, or a 5-6 membered heterocyclyl ring containing 1-2 heteroatoms selected from O, N, or S; wherein said $R^Y$ is independently and optionally substituted with 1-4 halo, CN, OR, or $C_{1-6}$alkyl;

each $R^{10}$ is independently selected from halo$C_{1-6}$alkyl, $C_{1-6}$ alkyl, halo, OR, C(=O)R, $CO_2R$, COCOR, $NO_2$, CN, S(O)R, $SO_2R$, SR, $N(R^4)_2$, $CON(R^4)_2$, $SO_2N(R^4)_2$, OC(=O)R, $N(R^4)COR$, $N(R^4)CO_2R$;

each $R^4$ is independently selected from H, $C_{1-6}$alkyl, or halo$C_{1-6}$alkyl;

each $R^5$ is independently selected from halo, halo$C_{1-6}$alkyl, or $C_{1-6}$alkyl; and each R is independently selected from H, $C_{1-6}$alkyl, or halo$C_{1-6}$alkyl.

One aspect of this invention provides compounds wherein Ht is

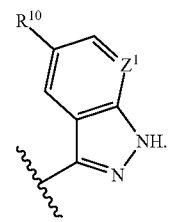

In some embodiments, $R^{10}$ is halo. In other embodiments, $R^{10}$ is fluoro. In some embodiments, $R^{10}$ is H or fluoro. In some embodiments, $R^{10}$ is H. In some embodiments, $Z^1$ is $CR^{10}$. In other embodiments, $Z^1$ is N.

Another embodiment provides compounds wherein $R^X$ is H or $C_{1-6}$ alkyl. In some embodiments, $R^X$ is H or $C_{1-4}$ alkyl. In some embodiments, the alkyl is methyl, ethyl, cyclopropyl, or isopropyl. In some embodiments, the alkyl is methyl. In some embodiments, the alkyl is independently and optionally substituted with 1-5 halo. In some embodiments, halo is fluoro. In some embodiments, $R^X$ is $C_{1-6}$ alkyl. In other embodiments, $R^X$ is H.

Another embodiment provides compounds wherein $R^Y$ is halo or $C_{1-6}$ alkyl. In some embodiments, $R^Y$ is methyl. In some embodiments, $R^y$ is H, chloro, methyl, 4-methyl piperazinyl, N-morphilinyl, or —$C(CH_3)_2OH$.

In some embodiments, $R^X$ is H or methyl and $R^Y$ is methyl. In other embodiments, $R^X$ is H and $R^Y$ is methyl. In yet other embodiments, $R^X$ is methyl and $R^Y$ is methyl.

Another embodiment provides compounds wherein $R^Y$ is a 5-6 membered heterocyclyl containing 1-2 heteroatoms selected from O, N, or S. In some embodiments, $R^Y$ is a 6-membered heterocyclyl containing 1-2 heteroatoms selected from O or N. In some embodiments, the heterocyclyl is morpholinyl, piperidinyl, or piperazinyl.

Another embodiment provides compounds wherein Ring D is a 5-10 membered cycloaliphatic or a 5-10 membered heterocyclyl where said heterocyclyl contains 1-2 heteroatoms selected from O, N, or S. In some embodiments, Ring D is 3-6 membered cycloaliphatic. In other embodiments, Ring D is 5-7 membered cycloaliphatic. In yet other embodiments, Ring D is cyclopropyl, cyclobutyl, cyclopentyl, cyclohexyl, cycloheptyl, or adamantly. In some embodiments, Ring D is cyclohexyl.

In some embodiments, Ring D is a 5-8 membered monocyclic or 8-10 membered bicyclic cycloaliphatic or heterocyclyl.

According to another embodiment, Ring D is a 5-7 membered heterocyclyl containing 1 heteroatom. In some embodiments, Ring D is a 6-membered heterocyclyl containing one oxygen atom (tetrahydropyran).

In yet another embodiments, Ring D is cyclopropyl, cyclobutyl, cyclopentyl, cyclohexyl, 4,4-difluoro-cyclohexyl, cycloheptyl, adamantly, or tetrahydro-2H-pyran-4-yl.

According to another embodiment, $R^5$ is halo or $C_{1-6}$alkyl.

In some embodiments, Ring D is optionally substituted with methyl or halo. In some embodiments, halo is fluoro.

In some embodiments, $Z^1$ is N, $R^{10}$ is F, and Ring D is a 5-7 membered cycloalkyl monocyclic ring.

In some embodiments, $R^X$ is H or $C_{1-6}$alkyl, $R^Y$ is H or $C_{1-6}$alkyl, $Z^1$ is CH or N, $R^{10}$ is halo, and Ring D is a 5-7 membered cycloalkyl monocyclic ring.

In some embodiments, the variables are as depicted in the compounds of Table 1.

One embodiment provides the compounds of Table 1 shown below.

TABLE 1

I-1

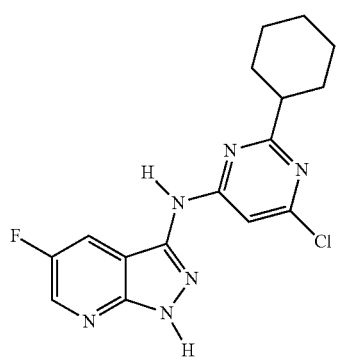 [SMILES: Fc1cnc2[nH]nc(Nc3cc(Cl)nc(C4CCCCC4)n3)c2c1]

TABLE 1-continued

I-2

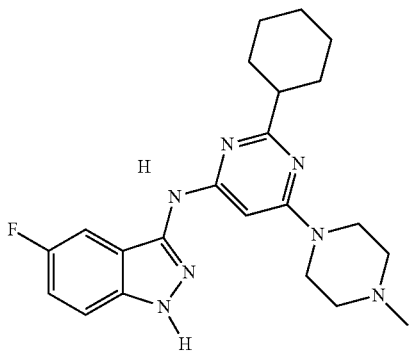

I-3

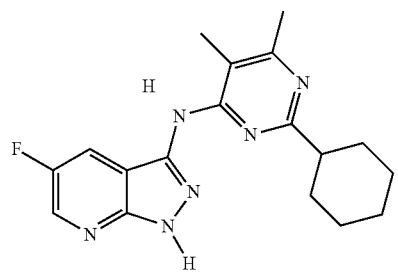

I-4

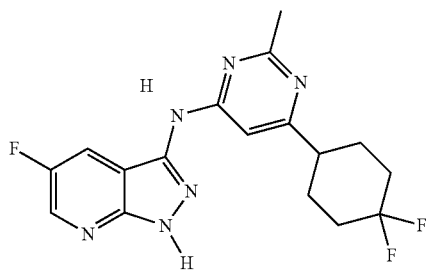

I-5

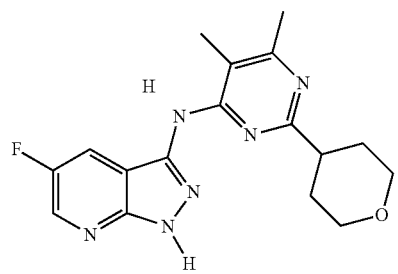

TABLE 1-continued
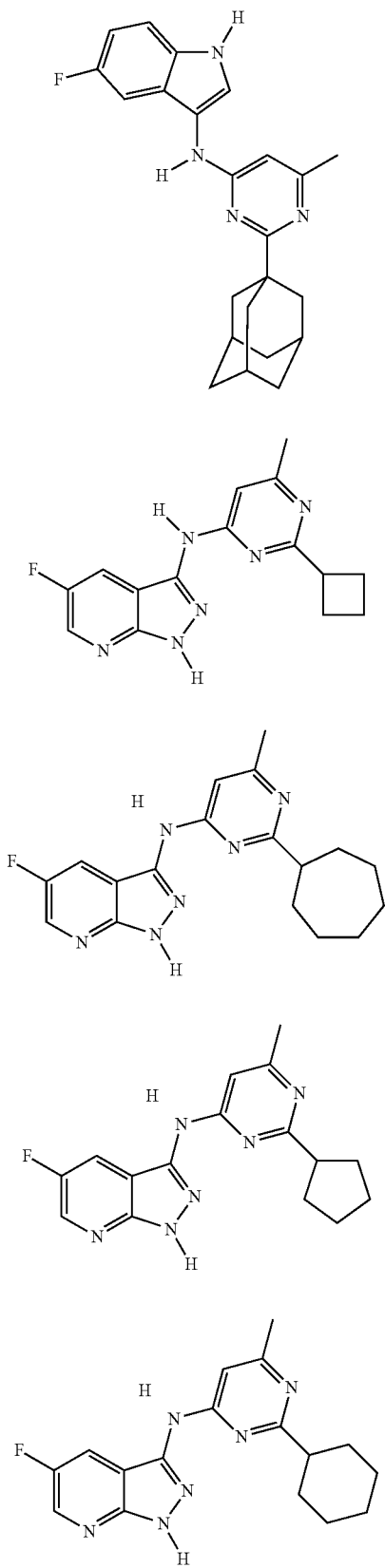
I-6
I-7
I-8
I-9
I-10
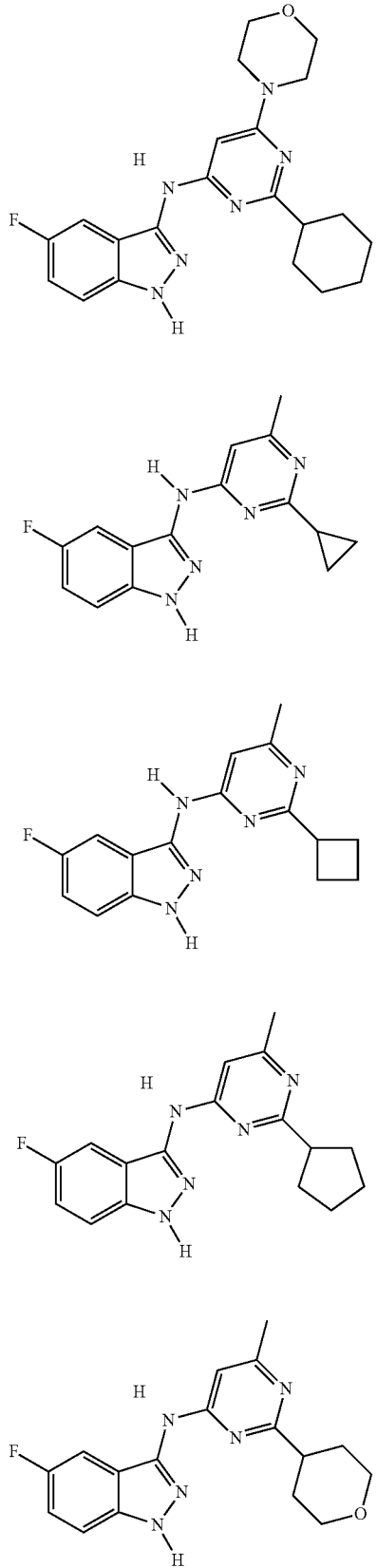
I-11
I-12
I-13
I-14
I-15

TABLE 1-continued

I-16
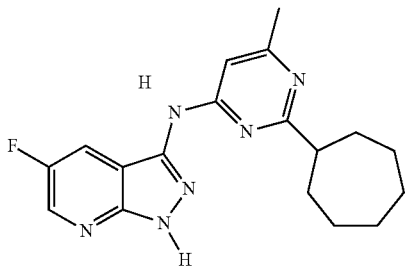

I-17
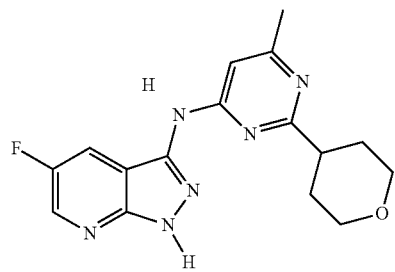

I-18
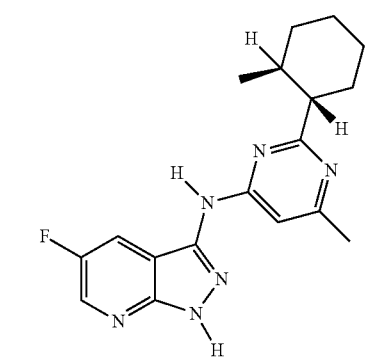 [SMILES: Cc1cc(Nc2n[nH]c3ncc(F)cc23)nc([C@H]2CCCC[C@@H]2C)n1]

I-19
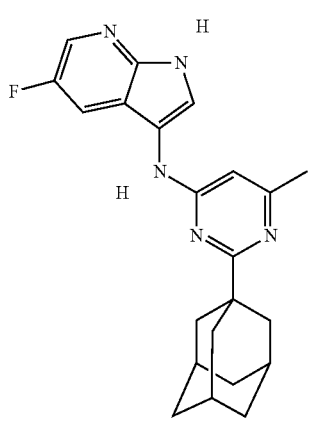

I-20
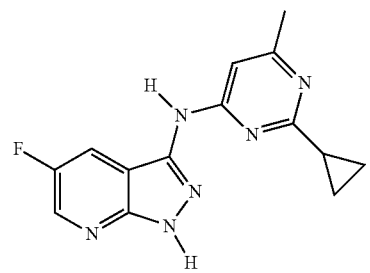 [SMILES: Cc1cc(Nc2n[nH]c3ncc(F)cc23)nc(C2CC2)n1]

I-21
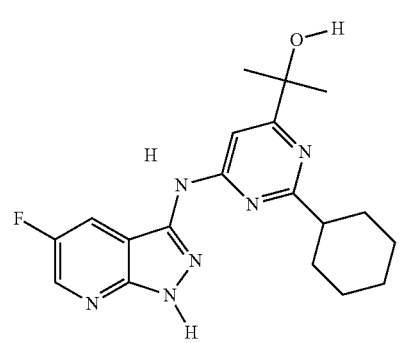

I-22
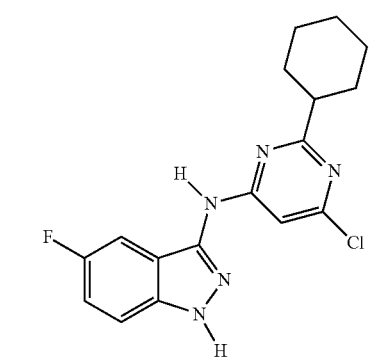 [SMILES: Fc1ccc2[nH]nc(Nc3cc(Cl)nc(C4CCCCC4)n3)c2c1]

I-23
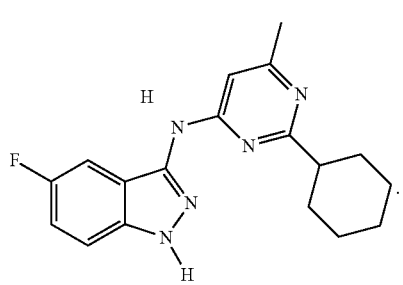

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) branched or unbranched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "alkyl" as used herein, means a straight-chain (i.e., unbranched), branched or unbranched, substituted or unsubstituted, hydrocarbon chain that is completely saturated and has a single point of attachment to the rest of the molecule. Unless otherwise specified, alkyl groups contain 1-6 alkyl carbon atoms. In some embodiments, alkyl groups contain 1-4 alkyl carbon atoms. In other embodiments, alkyl groups contain 1-3 alkyl carbon atoms. Examples include, but are not limited to, methyl, ethyl, isopropyl, n-propyl, sec-butyl, n-butyl, and n-pentyl.

The term "cycloaliphatic" (or "carbocycle" or "carbocyclyl" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, or phosphorus, (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, or tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired reactive sites in a multifunctional compound. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, an alkyl or aliphatic chain can be optionally replaced with another atom or group. Examples of such atoms or groups would include, but are not limited to, —NR—, —O—, —S—, —CO$_2$—, —OC(O)—, —C(O) CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein.

Unless otherwise specified, the optional replacements form a chemically stable compound. Optional replacements can occur both within the chain and at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a C$_3$ aliphatic can be optionally interrupted or replaced by —NR—, —C(O)—, and —NR— to form —NRC(O)NR— (a urea).

Unless otherwise specified, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention.

Unless otherwise indicated, a substituent can freely rotate around any rotatable bonds. For example, a substituent drawn as

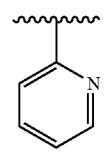

also represents

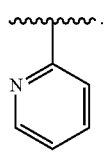

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It will also be appreciated that the compounds of the present invention can exist in free form for treatment, or where appropriate, as a pharmaceutically acceptable salt, salts, or mixtures thereof.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Base addition salts can be prepared by 1) reacting the purified compound in its acid form with a suitable organic or inorganic base and 2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

The following abbreviations are used:
DCM dichloromethane
EtOAc ethyl acetate
DMSO dimethyl sulfoxide
ATP adenosine triphosphate
DTT dithiothreitol
NMR nuclear magnetic resonance
HPLC high performance liquid chromatography
LCMS liquid chromatography-mass spectrometry
TLC thin layer chromatography
Rt retention time
RT room temperature
HEPES 4-(2-hydroxyethyl)-1-piperazine ethane-sulfonic acid
FBS fetal bovine serum
PVDF polyvinylidene fluoride
PEST phosphate buffered saline with Tween 20
TCF/LEF T cell factor/lymphoid enhancer factor
DIPEA diisopropylethylamine General Synthetic Methodology The compounds of this invention may be prepared in general by methods such as those depicted in the general schemes below, and the preparative examples that follow. Unless otherwise indicated, all variables in the following schemes are as defined herein.

Scheme 1

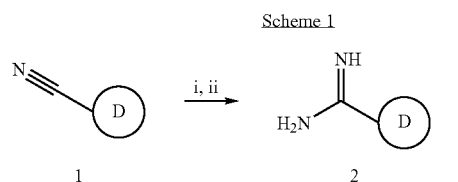

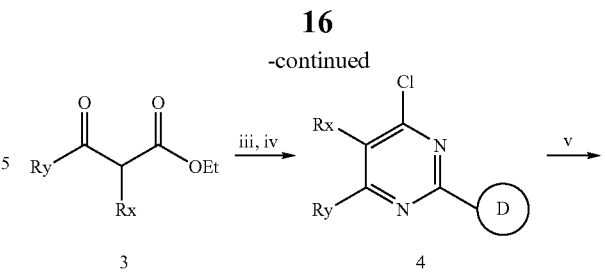

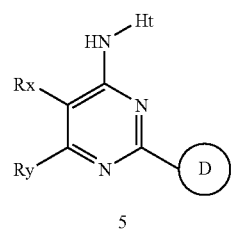

Reagents and conditions:
(i) HCl, Et$_2$O/MeOH,
(ii) NH$_3$, EtOH;
(iii) Et$_3$N, EtOH, reflux;
(iv) POCl$_3$, reflux;
(iv) NH$_2$Ht, DIPEA, NaI, DMF, 120° C.

Scheme 1 above shows a general synthetic route that is used for preparing the compounds 5. Compounds of formula 5 can be prepared from intermediate 1. The formation of amidine 2 is achieved by treating nitrile derivative 1 with HCl in the presence of methanol and then treating the intermediate imidate with NH$_3$ in ethanol. Intermediate 2 is then treated with the corresponding beta-ketoester reflux in EtOH. The corresponding hydroxypyrimidine intermediate is treated with POCl$_3$ to yield chloroderivative 4. This reaction is amenable to a variety of amidines 2. The chloropyrimidine 4 is treated with diverse amines like NH$_2$Ht in the presence of DIPEA and NaI to yield the final compound 5. This reaction is also amenable to a variety of heterocyclic amines like NH$_2$Ht.

Scheme 2

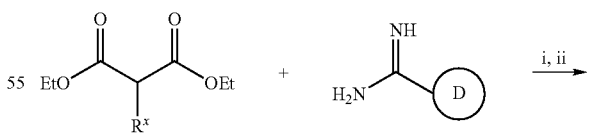

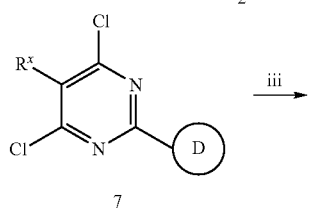

-continued

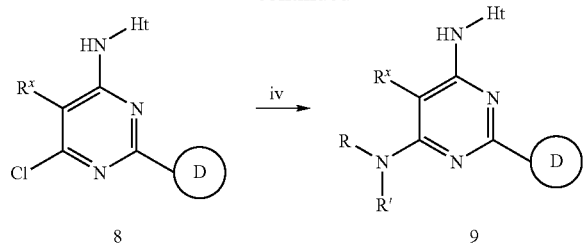

Reagents and conditions:
(i) EtONa, EtOH, reflux;
(ii) POCl₃, reflux;
(iii) HtNH₂, NaI, DMF, 110° C.
(iv) RR'NH, n-butanol, 108° C.

Scheme 2 above shows a general synthetic route that is used for preparing the compounds of formula 9. Compounds of formula 9 can be prepared from intermediate 7. The formation of intermediate 7 is achieved by reacting diethyl malonate with the corresponding amidine 2 in the presence of EtONa as a base in refluxing ethanol. The crude is then treated with POCl₃ to yield dichloropyrimidine intermediate 7. The dichloropyrimidine intermediate is sequentially treated with heterocyclic amines and other substituted amine derivatives to yield final compounds 9. These two reactions sequence are amenable to a variety of heterocyclic amines and a variety of substituted amines.

In Scheme II above, NRR', R and R', together with the nitrogen atom to which they are attached, form an optionally substituted 5-6 membered hetercyclic ring containing 1-2 heteroatoms selected from O, N, or S.

The present invention provides compounds and compositions that are useful as inhibitors of protein kinases. In some embodiments, the protein kinases are GSK-3 kinases.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said protein kinase inhibitor is a GSK-3 inhibitor.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

The term "biological sample" does not refer to in vivo samples.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Inhibition of GSK-3 activity has been linked to stem cell proliferation, cell differentiation, neuronal plasticity, and angiogenesis. These various functions are implicated in repair and regeneration. Inhibitors of GSK-3 have been shown to sustain self-renewal of embryonic stem cells, promote neuron, beta-cell, myeloid and osteoblast differentiation. (Sato et al, Nature Medicine 10, 55-63, 2004; Ding et al PNAS 100, 7632-37, 2003; Branco et al J Cell Science 117, 5731-37, 2004; Trowbridge et al, Nature Medicine 12, 89-98, 2006; Mussmann et al, JBC (Epub ahead of print) 2007; Kulkarni et al Journal of Bone and Mineral Res. 21, 910-920, 2006) With respect to neuronal plasticity, inhibition of GSK-3 has been shown to be important for regulating polarity, long-term potentiation (LTP) and neurite/axon growth (Hooper et al European J of Neuroscience 25, 81-86, 2007; Kim et al, Neuron 52, 981-996, 2006; Jiang et al Cell 120, 123-135, 2005). Inhibition of GSK-3 also has been shown to induce angiogenesis in endothelial cells (Skurk et al, Circulation Research 96, 308-318, 2005).

Accordingly, one aspect of this invention provides compounds that are useful in cell repair and regeneration. In some embodiments, said compounds are used to promote cell proliferation, cell differentiation, neuronal plasticity, or angiogenesis. In some embodiments, said compounds are chemomodulators of cell differentiation. In other embodiments, said compounds are chemomodulators of repair and regeneration.

In some embodiments, the compounds are used in increasing axonal and dendritic branching in neuronal cells. In some embodiments, the compounds are used to promote neuroplasticity. In other embodiments, the compounds are used to promote angiogenesis. In yet other embodiments, the compounds are used to promote neurogenesis. In yet other embodiments, the compounds are used to treat neuropsychiatric disorders, such as mania and depression.

Another embodiment provides compounds that are used to treat diabetes by promoting beta cell regeneration.

Yet another embodiment provides compounds that are used to treat osteoporosis by osteoblastogenesis.

GSK-3 functions as both a tyrosine and a serine/threonine kinase, similar to the DYRK kinase family. Like the DYRK kinase family, GSK-3 auto-phosphorylates a key tyrosine residue in its kinase domain (GSK-3a, Tyr 279 and GSK-3b, Tyr 216). This tyrosine phosphorylation has been shown to be important for positively modulating kinase activity. Lochead et al, demonstrated that this autophosphorylation occurs intramolecularly at a post-translationally intermediate step prior to maturation and is chaperones-dependent (Lochhead et al, *Molecular Cell* 24, (2006), pp. 627-633). After maturation, GSK-3 loses its tyrosine kinase activity and acts exclusively as a serine and threonine kinase towards exogenous substrates.

β-catenin is one of the exogenous serine/threonine substrates that GSK-3 phosphorylates. Inhibition of β-catenin phosphorylation leads to an increase in b-catenin levels that in turn translocate to the nucleus and transcriptionally control many genes involved in cellular response and function. One potential safety concern for GSK-3 inhibitors is that use of the inhibitors could lead to hyperproliferation via β-catenin induction. As primarily a serine/threonine kinase GSK-3 is central to many signaling pathways that control multiple cellular activities such as proliferation, differentiation and metabolism.

Accordingly, one aspect of this invention provides compounds that can partially attenuate GSK-3 activity without completely blocking the enzyme and affecting multiple substrates such as β-catenin. One embodiment provides compounds that selectively inhibit the tyrosine autophosphorylation form of the enzyme over the serine/threonine kinase form.

In some embodiments, said enzyme is GSK-3α; in other embodiments, GSK-3β. In some embodiments, said compounds that have a β-catenin:GSK-3β window of at least 4 fold and up to 400 fold. In some embodiments, the compounds have a β-catenin:GSK-3β window of at least 30 fold. In other embodiments, said compounds have a β-catenin:GSK-3α window of at least 35 fold and up to 600 fold.

Surprisingly, compounds that selectively inhibit the autophosphorylation of the tyrosine form of the GSK-3 enzyme relative to the serine/threonine kinase form promote neuron growth and dendrite formation, such as by increasing axonal and dendritic branching in neuronal cells. Increasing neuron growth and dendrite formation is advantageous and provides and unexpected and improved therapeutic efficacy when treating many types of degenerative conditions such as Stroke, Post stroke, Spinal Cord Injury, Traumatic Brain Injury, Alzheimer's, Parkinson's, Huntington's, Multiple Sclerosis, Amyotrophic Lateral Sclerosis, Diabetic Neuropathy, Charcot-Marie-Tooth, Leukocytopenia, Diabetes and Osteoporosis.

Compounds that selectively inhibit the auto-phosphorylation of the tyrosine form of the GSK-3 enzyme relative to the serine/threonine kinase form also promote angiogenesis, which is advantageous and provides an unexpected and improved therapeutic efficacy when treating many types of degenerative conditions such as the ones listed herein.

Another aspect provides compounds that are useful for the treatment of diseases, disorders, and conditions including, but not limited to, autoimmune diseases, inflammatory diseases, proliferative and hyperproliferative diseases, immunologically-mediated diseases, immunodeficiency disorders, immunomodulatory or immunosuppressive disorder, bone diseases, metabolic diseases, neurological and neurodegenerative diseases, neurotrophic factor, cardiovascular diseases, hormone related diseases, diabetes, allergies, asthma, and Alzheimer's disease. Another aspect of this invention provides compounds that are inhibitors of protein kinases, and thus are useful for the treatment of the diseases, disorders, and conditions, along with other uses described herein.

Another aspect provides pharmaceutically acceptable compositions comprising any of the compounds described herein and optionally comprising a pharmaceutically acceptable carrier, adjuvant or vehicle. In certain embodiments, these compositions optionally further comprise one or more additional therapeutic agents.

One aspect of this invention provides a method for the treatment or lessening the severity of a disease, disorder, or condition selected from an autoimmune disease, an inflammatory disease, a proliferative or hyperproliferative disease, such as cancer, an immunologically-mediated disease, an immunodeficiency disorders, a bone disease, a metabolic disease, a neurological or neurodegenerative disease, a cardiovascular disease, allergies, diabetes, asthma, Alzheimer's, disease, or a hormone related disease, comprising administering an effective amount of a compound, or a pharmaceutically acceptable composition comprising a compound, to a subject in need thereof.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer. In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease. In some embodiments, said disease is chosen from allergic or type I hypersensitivity reactions, asthma, diabetes, Alzheimer's disease, Huntington's disease, Parkinson's disease, AIDS-associated dementia, bipolar disorder, amyotrophic lateral sclerosis (ALS, Lou Gehrig's disease), multiple sclerosis (MS), schizophrenia, leukocytopenia, cardiomyocyte hypertrophy, reperfusion/ischemia, stroke, baldness, transplant rejection, graft versus host disease, rheumatoid arthritis, and solid and hematologic malignancies. In some embodiments, said disease is chosen from diabetes, bipolar disorder, schizophrenia, stroke, Huntington's disease, leukocytopenia and cardiomyocyte hypertrophy.

In other embodiments of this invention, said disease is a protein-kinase mediated condition. In some embodiments, said protein kinase in GSK-3.

The term "protein kinase-mediated condition", as used herein means any disease or other deleterious condition in which a protein kinase plays a role. Such conditions include, without limitation, autoimmune diseases, inflammatory diseases, proliferative and hyperproliferative diseases, immunologically-mediated diseases, immuno-deficiency disorders, immunomodulatory or immunosuppressive disorder, bone diseases, metabolic diseases, neurological and neurodegenerative diseases, cardiovascular diseases, hormone related diseases, diabetes, allergies, asthma, and Alzheimer's disease.

The term "GSK-3-mediated condition", as used herein means any disease or other deleterious condition in which GSK-3 plays a role. Such conditions include, without limitation, diabetes, diabetic neuropathy, osteoporosis, Alzheimer's disease, Huntington's disease, Parkinson's disease, AIDS-associated dementia, bipolar disorder, amyotrophic lateral sclerosis (ALS, Lou Gehrig's disease), multiple sclerosis (MS), schizophrenia, leukocytopenia, cardiomyocyte hypertrophy, stroke, spinal cord injury, traumatic brain injury, Charcot-Marie-Tooth, and rheumatoid arthritis.

In some embodiments, said disease is a degenerative condition. In some embodiments, said degenerative condition is chosen from stroke, Alzheimer's Disease, Parkinson's Disease, Huntington's Disease, Amyotrophic Lateral Sclerosis (ALS), multiple sclerosis (MS), spinal cord injury, traumatic brain injury, Charcot-Marie-Tooth, leukocytopenia, diabetes, diabetic neuropathy, and osteoporosis.

In some embodiments, said disease is a neurodegenerative condition. In another embodiment, said neurodegenerative conditions is selected from stroke, Alzheimer's disease, Parkinson's disease, Huntington's disease, Amyotrophic Lateral Sclerosis (ALS), multiple sclerosis (MS), spinal cord injury, traumatic brain injury, and Charcot-Marie-Tooth.

One embodiment provides a method increasing axonal and dendritic branching in neuronal cells comprising the step of contacting said cells with a compound described herein. Another embodiment provides a method of promoting neuroplasticity comprising the step of contacting said cells with a compound described herein. Another embodiment provides a method of promoting angiogenesis comprising the step of contacting said cells with a compound described herein. Yet another embodiment provides a method of treating neuropsychiatric disorders, such as mania and depression, comprising administering to a patient a compound described herein.

According to one aspect of the invention, said neurodegenerative disease is stroke. In some embodiments, the compounds are used to treat stroke patients during stroke recovery. In some cases, the compounds are used in post-stroke administration. The length of treatment can range from 1 month to one year. In some embodiments, the compound is administered after the stroke has occurred. In some embodiments, said administration occurs immediately after ischemia. In other embodiments, said administration occurs 48 hours after ischemia to 6 months after ischemia. In some embodiments, the compounds are used in combination with other forms of stroke recovery treatment, such as physical therapy.

Another embodiment provides a method of treating diabetes comprising the step of contacting a beta cell with a compound described herein. In some embodiments, the compound promotes beta cell regeneration.

Another embodiment provides a method of treating osteoporosis comprising the step of contacting a bone cell with a compound described herein. In some embodiments, said compound promotes osteoblastogenesis in the cell.

It will also be appreciated that certain of the compounds of present invention can exist in free form for treatment, or where appropriate, as a pharmaceutically acceptable salt or pharmaceutically acceptable derivative thereof.

It should be understood that this invention includes mixtures/combinations of different pharmaceutically acceptable salts and also mixtures/combinations of compounds in free form and pharmaceutically acceptable salts.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is a GSK-3-mediated condition. In some embodiments, a GSK-3-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, a GSK-3-mediated condition) comprising the step of administering to a patient one of the above-described pharmaceutical compositions. The term "patient", as used herein, means an animal, preferably a human.

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, Parkinson's Disease, Huntington's Disease, Amyotrophic Lateral Sclerosis (ALS), multiple sclerosis (MS), spinal cord injury, traumatic brain injury, Charcot-Marie-Tooth, leukocytopenia, diabetic neuropathy, osteoporosis, cystic fibrosis, and viral disease, or any specific disease described above.

Another aspect of the invention relates to inhibiting protein kinase activity in a patient, which method comprises administering to the patient a compound of formula I or a composition comprising said compound.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

In some embodiments, said protein kinase inhibitor is a GSK-3 kinase inhibitor.

This invention may also be used in methods other than those involving administration to a patient.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyz-

EXAMPLES

As used herein, the term "Rt(min)" refers to either HPLC or LCMS retention time, in minutes, associated with the compound.

Unless otherwise indicated, the HPLC method utilized to obtain the reported retention time is as follows:

Column: ACE C8 column, 4.6×150 mm

Gradient: 0-100% acetonitrile+methanol 60:40 (20 mM Tris phosphate)

Flow rate: 1.5 mL/minute

Detection: 225 nm.

LCMS (Liquid Chromatography Mass Spectrometry) samples were analyzed on a MicroMass Quattro Micro mass spectrometer operated in single MS mode with electrospray ionization. Samples were introduced into the mass spectrometer using chromatography. Mobile phase for all mass spec. analysis consisted of acetonitrile-water mixtures with either 0.2% formic acid or 0.1% TFA as a modifier. Column gradient conditions are 10%-90% acetonitrile over 3 mins gradient time and 5 mins run time on a Waters YMC Pro-C18 4.6×50 mm column. Flow rate is 1.5 ml/min.

$^1$H-NMR spectra were recorded at 400 MHz using a Bruker DPX 400 instrument. The following compounds of formula I were prepared and analyzed as follows.

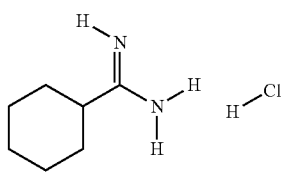

Intermediate 1

Cyclohexanecarboximidamide Hydrochloride

The temperature of a mixture of cyclohexane carbonitrile (60 g, 550 mmol, 1 eq) in Et$_2$O (150 ml) and MeOH (33 ml) was lowered to 0° C. before HCl (g) was bubbled through for 20 min. The reaction mixture was then removed to the fridge O/N. The resulting white solid was suspended in Et2O and filtered to give the methyl cyclohexanecarbimidate intermediate (125.1 g, 128%). This crude solid was suspended in a mixture of EtOH (400 ml)/2M NH$_3$ in EtOH (100 ml) at 0° C. before NH3(g) was bubbled through the suspension for 2 h. The reaction mixture was then placed in the fridge O/N. The resulting solid was filtered and washed with MeOH to yield a filtrate which was then concentrated in-vacuo. The residue was taken up in MeOH and concentrated in-vacuo until a solid began to precipitate at which time Et2O was added. The resulting solid then formed was filtered to give a sticky solid that was placed into the vac-oven O/N to yield the desired product as a white solid (87.80 g, 98%). 1H (400 MHz, DMSO) 1.00-1.88 (10H, m), 2.35-2.57 (1H, m), 8.86-9.02 (3H, m).

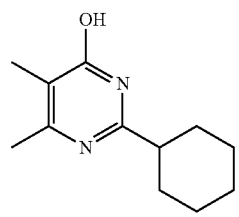

Intermediate 2

2-cyclohexyl-5,6-dimethylpyrimidin-4-ol

A solution of sodium ethoxide (previously prepared by dissolving sodium (6.36 g, 278 mmol, 3 eq) in EtOH (300 ml)), stirring at RT, was treated with ethyl 2-methyl-3-oxobutanoate (16.94 ml, 120 mmol, 1.3 eq). A slurry of cyclohexanecarboximidamide hydrochloride (15 g, 92 mmol, 1 eq) in EtOH (100 ml) was then added and the RM heated at reflux for 8 h. The RM was concentrated, water added and the pH adjusted to ~7-8 with 2N HCl. Following acidification a white solid precipitated and this was filtered and dried in the vac-oven to yield 2-cyclohexyl-5,6-dimethylpyrimidin-4-ol as a white solid (28.91 g, 151%). 1H (400 MHz, DMSO) 1.03-1.86 (10H, m), 1.96 (3H, s), 2.16 (3H, s), 2.36-2.57 (1H, m), 12.05 (1H, brs); ES+207.

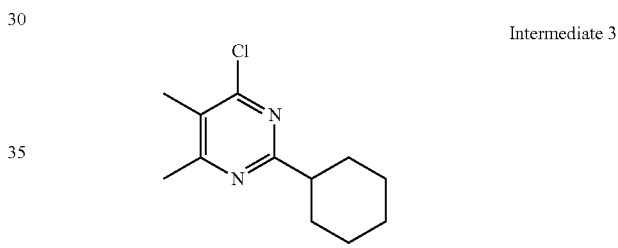

Intermediate 3

4-chloro-2-cyclohexyl-5,6-dimethylpyrimidine

POCl$_3$ (220 ml, 2.4 mol, ~26 eq) was cooled to ~–50° C. before being carefully treated with 2-cyclohexyl-5,6-dimethylpyrimidin-4-ol (28.9 g, '92 mmol', 1 eq). The cooling bath was then removed and the pot allowed to warm to RT followed by heating to reflux for 6 h. The RM was concentrated, treated with ice and saturated NaHCO$_3$ and extracted into Et2O before being dried (sodium sulfate)/concentrated. The resulting oil was subjected to column chromatography using EtOAc (10%): 40-60 Petrols (90%) as eluent to yield 4-chloro-2-cyclohexyl-5,6-dimethylpyrimidine as an oil (5.7011 g, 28% over first two steps). 1H (400 MHz, DMSO) 1.16-1.90 (10H, m), 2.26 (3H, s), 2.46 (3H, s), 2.60-2.75 (1H, m). ES+225.

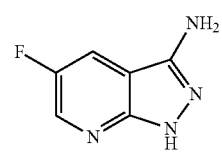

Intermediate 4

The overall synthetic scheme for the synthesis of 5-fluoro-1H-pyrazolo[3,4-b]pyridin-3-amine 5 is depicted below.

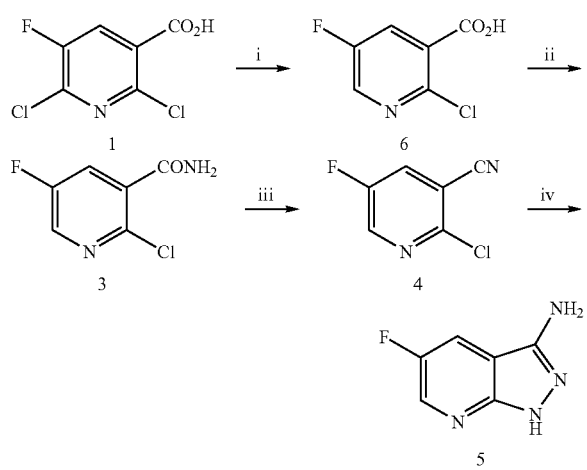

Reagents and conditions:
i. Pd (OAc)₂, PPh₃, Et₃N, H₂CO₂;
ii. 1) (COCl)₂, CH₂Cl₂, cat. DMF;
   2) NH₃ (g), dioxane,
iii. TFAA, Et₃N, CH₂Cl₂, 0° C.;
iv. H₂NNH₂•H₂O, n-butanol, reflux

2-Chloro-5-fluoronicotinic acid (6)

To a round-bottomed flask under a N₂ atmosphere were added degassed DMF (270 mL), Pd(OAc)₂ (0.05 eq, 2.7 g, 11.9 mmol), PPh₃ (0.1 eq, 6.2 g, 23.8 mmol), and degassed Et₃N (6 eq, 200 mL, 1428.6 mmol). The mixture was stirred for 20 minutes, HCOOH (3 eq, 28 mL, 714.3 mmol) was then added. 5 minutes later, 2,6-dichloro-5-fluoronicotinic acid (50 g, 238.1 mmol) was added. The mixture was stirred at 50° C. The reaction was followed by analysis (1H NMR) of a worked-up aliquot. When all starting material was consumed (24 h), the mixture was cooled to 0° C. and water (500 mL) was added. After 20 minutes. The mixture was filtered through a pad of Celite that was rinsed with water. The mixture was basified to pH 9 with 30% aq. NaOH and washed with EtOAc (2×). HCl (12 N) was added slowly to pH 1 and the solution was saturated with NaCl. The mixture was extracted with EtOAc (3×). The combined organic extracts were washed with brine, dried (Na₂SO₄), and concentrated under reduced pressure to give 37 g (88%) of a beige solid used in the next step without further purification.

¹H NMR (DMSO-d₆, 300 MHz): δ 8.16 (dd, 1H); 8.58 (d, 1H).

2-Chloro-5-fluoronicotinamide (3)

To a solution of 2-chloro-5-fluoronicotinic acid 6 (50 g, 285 mmol) and DMF (2 mL, 28 mmol) in DCM (400 mL) at 0° C. was added oxalyl chloride (64 mL, 741 mmol) dropwise. The reaction mixture was stirred at room temperature overnight and concentrated in vacuo. The resulting yellow liquid was dissolved in 1,4-dioxane (600 mL), cooled at 0° C. and NH₃ (g) was bubbled through the solution for 30 minutes. The mixture was stirred at room temperature overnight. The resulting mixture was filtered and the filtrate was concentrated to give compound 3 (44 g, 89%) as a beige solid. ¹H NMR (DMSO-d₆, 300 MHz): δ 7.84 (s, 1H), 7.96 (dd, 1H), 8.09 (s, 1H), 8.49 (d, 1H).

2-Chloro-5-fluoronicotinonitrile (4)

A suspension of crude compound 3 (65 g, 372.4 mmol) and Et3N (114 mL, 819.2 mmol) in DCM (700 mL) was cooled to 0° C. and TFAA (57 mL, 409.6 mmol) was added dropwise. The resulting yellow solution was stirred for 90 minutes at 0° C., diluted with DCM, washed with sat. aq. NaHCO₃ and brine, and dried (Na₂SO₄). The mixture was filtered and concentrated. Kugel Rohr distillation of the residue (~70° C./1 mbar) gave 50 g (86%) of compound 4 as a beige solid.

Compound 4 can also be purified by column chromatography (SiO₂, 8:1 heptane: EtOAc). ¹H NMR (CDCl₃, 300 MHz): δ 7.78 (dd, 1H); 8.49 (d, 1H).

5-Fluoro-1H-pyrazolo[3,4-b]pyridin-3-amine (5)

To a solution of compound 4 (50 g, 321.7 mmol) in 1-butanol (1 L) was added hydrazine monohydrate (150 mL, 3.2 mol), and the mixture was refluxed for 4 h. The mixture was cooled to room temperature and concentrated. The precipitate was successively washed on filter with water (2×) and Et₂O (2×) and dried in vacuo overnight to give compound 5 (44 g, 88%) as a yellow solid. ¹H NMR (DMSO-d₆, 300 MHz): δ 5.53 (s, 2H); 7.94 (dd, 1H); 8.35 (dd, 1H); 12.02 (s, 1H).

Example 1

(I-3)

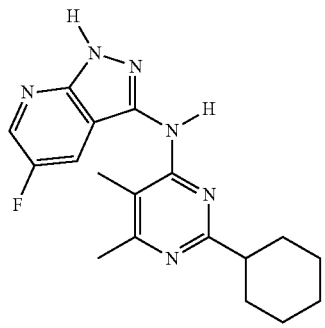 [SMILES: Cc1nc(C2CCCCC2)nc(Nc2n[nH]c3ncc(F)cc23)c1C]

(N-(2-cyclohexyl-5,6-dimethylpyrimiidin-4-yl)-5-fluoro-1H-pyrazolo[3,4-b]pyridin-3-amine A solution of 4-chloro-2-cyclohexyl-5,6-dimethylpyrimidine (5.70 g, 25.4 mmol, 1 eq) in NMP (50 ml), stirring at RT, was treated with 5-fluoro-1H-pyrazolo[3,4-b]pyridin-3-amine (4.63 g, 30.4 mmol, 1.2 eq). The RM was heated at 130° C. for 4 h before being cooled to RT. The RM was diluted with EtOAc/water and the organics were washed with sNaHCO3 and further water. During work up a solid was produced and this was filtered. Treatment of the solid with DCM/MeOH/40-60-petrols produced (N-(2-cyclohexyl-5,6-dimethylpyrimiidin-4-yl)-5-fluoro-1H-pyrazolo[3,4-b]pyridin-3-amine which was isolated as a white solid. The solid was dried in a vac-oven @80° C. O/N to yield VRT-763633 (Lot2) as a white solid (5.2608 g, 61%).). 1H (400 MHz, DMSO) 0.87-1.22 (5H, m), 1.40-1-62 (5H, m), 2.04 (3H, s), 2.20 (3H, s), 2.25 (1H, quin), 7.67 (1H, dd), 8.40 (1H, dd), 8.91 (1H, s), 13.13 (1H, s). ES+341, ES−339.

The following compounds were made in a manner similar to the manner described above.

Compounds I-3 to I-10 and I-12 to I-21 were made according to method described in Scheme I and the method described for making Example 1.

Compounds I-1, I-2, I-11, and I-22 were made according to the method described in Scheme II.

Table 2 below describes analytical data associated with compounds shown in Table 1.

TABLE 2

| Cmpd # | M + 1 (obs) | LCMS Rt (min) | NMR |
|---|---|---|---|
| I-1 | 347 | 3.92 | (400 MHz, DMSO) 1.10-1.96 (10H, m), 2.56-2.69 (1H, m), 7.65 (1H, brs), 8.27-8.39 (1H, m), 8.58 (1H, s), 10.72 (1H, s), 13.34 (1H, s). |
| I-2 | 410 | 4.07 | (400 MHz, DMSO) 1.14-1.93 (10H, m), 2.19 (3H, s), 2.32-2.56 (5H, m), 3.49-3.59 (4H, m), 7.00 (1H, brs), 7.18-7.30 (1H, m), 7.36-7.47 (1H, m), 7.83-7.95 (1H, m), 9.63 (1H, s), 12.44 (1H, s). |
| I-3 | 341.57 | 3.63 | (DMSO) 0.87-1.22 (5H, m), 1.40-1-62 (5H, m), 2.04 (3H, s), 2.20 (3H, s), 2.25 (1H, quin), 7.67 (1H, dd), 8.40 (1H, dd), 8.91 (1H, s), 13.13 (1H, s). |
| I-4 | 363 | 3.42 | (400 MHz, DMSO) 1.77-2.14 (8H, m), 2.35 (3H, s), 2.75-2.87 (1H, m), 7.41 (1H, brs), 8.26-8.38 (1H, m), 8.52-8.62 (1H, m), 10.22 (1H, s), 13.22 (1H, s). |
| I-5 | 343 | 2.98 | (400 MHz, DMSO) 1.44-1.67 (4H, m), 2.18 (3H, s), 2.35 (3H, s), 2.59-2.70 (1H, m), 3.22-3.37 (2H, m), 3.71-3.82 (2H, m), 7.73-7.83 (1H, m), 8.52-8.59 (1H, m), 9.10 (1H, s), 13.33 (1H, s). |
| I-6 | 378 | 4.07 | (400 MHz, DMSO) 1.64-1.80 (6H, m), 1.94-2.12 (9H, m), 2.32 (3H, s), 7.19-7.55 (3H, m), 7.75-7.87 (1H, m), 9.81 (1H, s), 12.56 (1H, s). |
| I-7 | 299 | 3.17 | (400 MHz, DMSO) 1.74-1.86 (1H, m), 1.91-2.05 (1H, m), 2.16-2.27 (2H, m), 2.30-2.43 (5H, m), 3.49-3.62 (1H, m), 7.38 (1H, brs), 8.30-8.41 (1H, m), 8.52-8.62 (1H, m), 10.24 (1H, s), 13.20 (1H, s). |
| I-8 | 341 | 3.73 | (400 MHz, DMSO) 1.38-1.81 (10H, m), 1.85-1.97 (1H, m), 2.33 (3H, s), 2.73-2.84 (1H, m), 7.25-7.41 (1H, m), 8.29-8.38 (1H, m), 8.49-8.60 (1H, m), 10.11 (1H, s), 13.15 (1H, s). |
| I-9 | 313 | 3.32 | (400 MHz, DMSO) 1.52-2.00 (8H, m), 2.33 (3H, s), 3.04-3.16 (1H, m), 7.36 (1H, brs), 8.25-8.41 (1H, m), 8.49-8.62 (1H, m), 10.17 (1H, s), 13.19 (1H, s). |
| I-10 | 327.4 | 1.72 | H NMR (500 MHz, MeOD) 8.54 (s, 1H), 8.22 (s, 1H), 2.80(m, 1H), 1.9-1.1(m, 10H) |
| I-11 | 397 | 4.02 | (400 MHz, DMSO) 1.12-1.94 (10H, m), 2.42-2.55 (1H, m), 3.46-3.55 (4H, m), 3.65-3.73 (4H, m), 7.00 (1H, brs), 7.18-7.29 (1H, m), 7.38-7.47 (1H, m), 7.85-7.93 (1H, m), 9.67 (1H, s), 12.44 (1H, s). |
| I-12 | 284 | 3.19 | (400 MHz. DMSO) 0.83-1.00 (4H, m), 1.93-2.04 (1H, m), 7.18-7.34 (2H, m), 7.42-7.52 (1H, m), 7.68-7.80 (1H, m), 9.86 (1H, s), 12.54 (1H, s). |
| I-13 | 298 | 3.33 | (400 MHz, DMSO) 1.75-1.87 (1H, m), 1.91-2.05 (1H, m), 2.16-2.26 (1H, m), 2.31-2.45 (5H, m), 3.49-3.62 (1H, m), 7.19-7.53 (3H, m), 7.75-7.88 (1H, m), 10.02 (1H, s), 12.57 (1H, s). |
| I-14 | 312 | 3.48 | (400 MHz, DMSO) 1.52-2.00 (8H, m), 2.32 (3H, s), 3.03-3.15 (1H, m), 7.20-7.54 (3H, m), 7.72-7.87 (1H, m), 9.96 (1H, s), 12.57 (1H, s). |
| I-15 | 328 | 3.13 | (400 MHz, DMSO) 1.80-1.97 (4H, m), 2.39 (3H, s), 2.85-2.97 (1H, m), 3.36-3.54 (2H, m), 3.93-4.06 (2H, m), 7.26-7.37 (1H, m), 7.41-7.59 (2H, m), 7.77-7.90 (1H, m), 10.06 (1H, s), 12.65 (1H, s). |
| I-16 | 355 | 3.75 | (400 MHz, DMSO) 1.26-1.67 (10H, m), 1.71-1.83 (2H, m), 2.18 (3H, s), 2.34 (3H, s), 2.55-2.66 (1H, m), 7.75-7.89 (1H, m), 8.50-8.59 (1H, m), 9.00-9.15 (1H, m), 13.26 (1H, s). |
| I-17 | 329 | 2.87 | (400 MHz., DMSO) 1.75-1.85 (4H, m), 2.35 (3H, s), 2.79-2.91 (1H, m), 3.31-3.48 (2H, m), 3.87-3.97 (2H, m), 7.40 (1H, brs), 8.24-8.39 (1H, m), 8.54-8.63 (1H, m), 10.21 (1H, s), 13.22 (1H, s). |
| I-18 | 341.4 | 1.79 | H NMR (500 MHz, DMSO-d6) 13.73 (s, H), 8.64 (s, 1H), 8.25 (s, 1H), 1.89-1.1(m12, H), 0.85 (d, J = 7.9 Hz, 3H), 0.74 (d, J = 12.7 Hz, 1H). |
| I-19 | 379 | 4.01 | (400 MHz, DMSO) 1.63-1.78 (6H, m), 1.84-2.06 (9H, m), 2.34 (3H, s), 7.30 (1H, brs), 8.27-8.39 (1H, m), 8.52-8.62 (1H, m), 10.03 (1H, s), 13.19(1H, s). |
| I-20 | 285 | 3.03 | (400 MHz, DMSO) 0.88-0.98 (4H, m), 1.94-2.04 (1H, m), 2.30 (3H, s), 7.30 (1H, s), 8.25-8.35 (1H, m), 8.54-8.62 (1H, m), 10.07 (1H, s), 13.17 (1H, s). |
| I-21 | 371.58 | 3.76 | (DMSO) 1.20-1.39 (3H, m), 1.40 (6H, s), 1.50-1.61 (2H, m), 1.63-1.92 (5H, m), 2.63 (1H, quin), 5.15 (1H, s, OH), 7.14 (1H, br s), 8.33 (1H, dd), 8.56 (1H, dd), 10.12 (1H, s), 13.18 (1H, s). |
| I-22 | 346 | 4.02 | (400 MHz, DMSO) 1.12-1.96 (10H, m), 2.55-2.69 (1H, m), 7.22-7.32 (1H, m), 7.44-7.92 (3H, m), 10.57 (1H, s), 12.70 (1H, s). |

TABLE 2-continued

| Cmpd # | M + 1 (obs) | LCMS Rt (min) | NMR |
|---|---|---|---|
| I-23 | 326.4 | 1.94 | H NMR (500 MHz, DMSO-d6) 13.12 (s, 1H), 11.58 (s, 1H), 7.68 (s, 1H), 7.58 (dd, J = 4.2, 8.9 Hz, 1H), 7.32 (t, J = 9.0 Hz, 1H), 2.80 (s, 1H), 1.92-1.05(m, 10H). |

Example 2

GSK-3 Inhibition Assay

Compounds of the present invention were screened for their ability to inhibit GSK-3β (AA 1-420) activity using a standard coupled enzyme system (Fox et al., *Protein Sci.* 1998, 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of the present invention. The assay stock buffer solution (175 µl) was incubated in a 96 well plate with 5 µl of the test compound of the present invention at final concentrations spanning 0.002 µM to 30 µM at 30° C. for 10 min. Typically, a 12-point titration was conducted by preparing serial dilutions (from 10 mM compound stocks) with DMSO of the test compounds of the present invention in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration. Compounds of the invention were found to inhibit GSK-3.

The following compounds were found to inhibit GSK-3 at a Ki value of <25 nM: I-1, I-3, I-4, I-8 to I-10, I-14, I-16 to I-19, I-21 to I-23.

The following compounds were found to inhibit GSK-3 at a Ki value of <500 nM and ≥25 nM: I-2, I-5 to I-7, I-11 to I-13, I-15, and I-20.

Example 3

GSK-3α and GSK3β p-TYR Inhibition Assay

Compounds are screened for their ability to inhibit the phosphorylation of tyrosine (TYR) residues through the use of western blotting of Jurkat cells dosed with the compounds. The phosphorylation of the specific TYR residues tested are GSK3α TYR 279 and GSK3β TYR 216.

Preparation of Cells and Lysates

Jurkat cells are seeded at a density of $2\times10^5$ cells/well in a 12 well dish in starvation media (RPMI+1% FBS+P/S). Following starvation for 16 hours, the compound is dosed into each well at a final DMSO concentration of 0.3% and cells are incubated o/n at 37° C. 5% $CO_2$. The next day, cells are spun down at 1500 rpm, washed with PBS, and lysed in 100 uL Laemli sample buffer with β-mercaptoethanol.

Western Blot Protocol 15 microliters (uL) of cell lysates are loaded onto a 10% tris-glycine gel and run at 120 v for 2 hours or until dye front runs off of the gel. The protein is then transferred onto a PVDF membrane at 100 v for 60 min. PBST (PBS containing 0.1% Tween 20, such as 1 ml Tween per 1 L of PBS) is then made up and used for all washes and antibody incubations. The blot is blocked in 5% nonfat milk PBST for one hour.

The primary antibody (GSK-3α/β pTYR 279/216 at 1:1000 dilution Upstate cat #05-413) is then added in 5%-nonfat milk PBST overnight at 4° C. with gentle rocking. The blot is then washed in PBST for 5 min. This is then repeated 4 times. A secondary anti-mouse-HRP conjugated antibody (1:5000 dilution) is added for 60 min in 5% milk PBST. The blot is then washed in PBST for 5 min. This is also repeated 4 times. 3.0 mL of the developing solution (ECL plus Western Blotting Detection System from Amersham/GE cat # RPN2132) is made and then added. The solution is swirled over the blot for ~30 sec. The blot is then developed using CL-Xposure clear blue X-ray film. GAPDH expression level is used as a loading control, (GAPDH antibody: santa cruz 25-778) at 1:10000 dilution.

For determination of GSK-3α and GSK-3β pTYR IC50, the density of the respective bands for each protein at specific compound concentration is compared to a no compound DMSO treated control cell sample present on each exposure. IC50 numbers are defined as the concentration of compound in which the density of the GSK-3α or GSK-3β band is 50% of the no compound control.

Example 4

β-Catenin Stabilization Protocol

GSK-3 phosphorylation of β-catenin targets it to the proteosome for degradation. Inhibition of GSK-3 results in accumulation of β-catenin in the cytosol of cells which through interaction with the transcription factor TCF/LEF translocates to the nucleus and drives the transcription of Wnt-dependent genes. The assay is designed to determine the level of β-catenin dependent TCF/LEF transcriptional activity in a quantitative manner through the use of a β-lactamase reporter assay in Jurkat cells dosed with a compound.

Jurkat β-catenin cells are starved overnight in assay media (1% FBS, 1× Penstrep, RPMI) in the flask. The next day Jurkat β-catenin cells are seeded in 96 well flat bottom plates at a density of 50,000 cells/well in assay media in a volume of 100 ul. The compound is added to the well at a final DMSO concentration of 0.75% and incubated at 37° C. o/n. The next day, 20 uL of 6× CCF4 dye is added to the wells and incubated at room temperature for 1-2 hours. Plates are read on the Cytofluor 4000 series multiwell plate reader and the 460/530 ratio is determined. The GSK-3 IC50 for induction of β-catenin is determined by plotting the 460/530 ratio against the concentration of compound (Log scale) and using the equation of the slope to calculate the point at which the ratio is 50% of the maximum effect.

β-catenin:GSK-3 windows were calculated by dividing the β-catenin IC50 value obtained in Example 4 by the GSK-3α or GSK3β p-TYR IC50 value obtained in Example 3.

The following compounds were found to have a β-catenin: GSK-3α windows between 35 and 500 fold: I-4, I-5, I-15, I-17, and I-21. The following compounds were found to have a β-catenin:GSK-3α window between 500 and 2000 fold: I-8 to I-10, I-16, I-19, and I-23. The following compounds were found to have a β-catenin:GSK-3α window between 2000 and 6000: I-3 and I-18.

The following compounds were found to have a β-catenin: GSK-3β window between 4 and 25 fold: I-4, I-15, I-17, and I-18. The following compounds were found to have a β-catenin:GSK-3β window between 25 and 100 fold: I-8 to I-10, I-16, I-21, and I-23. The following compounds were found to have a β-catenin:GSK-3β window between 100 and 400 fold: I-3, I-5, and I-19.

Table 3 shows GSK-3α pTYR, GSK-3β pTYR, and β-catenin IC50 data for select compounds of Table 1.

TABLE 3

| Compound Number | GSK3a pTYR 279: IC50: uM) | GSK3b pTYR 216: IC50: (uM) | Beta Catenin IC50: (uM) |
| --- | --- | --- | --- |
| I-3 | 0.0007 | 0.013 | 3.7 |
| I-4 | 0.001 | 0.02 | 0.21 |
| I-5 | 0.03 | 0.8 | >10 |
| I-8 | 0.0003 | 0.01 | 0.6 |
| I-9 | 0.002 | 0.048 | 1.4 |
| I-10 | 0.0005 | 0.006 | 0.4 |
| I-15 | 0.03 | 0.2 | 4.83 |
| I-16 | 0.003 | 0.083 | 3.7 |
| I-17 | 0.003 | 0.03 | 0.11 |
| I-18 | 0.001 | 0.3 | 2.4 |
| I-19 | 0.002 | 0.02 | 3.32 |
| I-21 | 0.003 | 0.02 | 1 |
| I-23 | 0.002 | 0.025 | 1.1 |

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:

1. A compound of formula I:

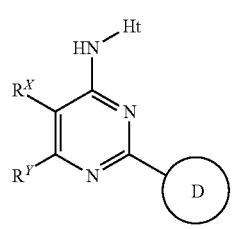

or a pharmaceutically acceptable salt thereof, wherein:
Ht is

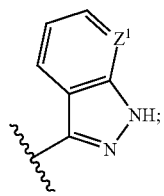

wherein any substitutable carbon on Ht is independently and optionally substituted with —$R^{10}$; Ring D is a 3-10 membered cycloaliphatic wherein the cycloaliphatic is independently and optionally substituted with 1-5 —$R^5$;

$Z^1$ is N, CH, or $CR^{10}$;

$R^X$ is H, halo, or $C_{1-6}$alkyl, wherein the alkyl is independently and optionally substituted with 1-5 groups selected from halo, —CN, and —OR;

$R^Y$ is H, halo, $C_{1-6}$alkyl, or a 5-6 membered heterocyclyl ring containing 1-2 heteroatoms selected from O, N, or S; wherein said $R^Y$ is independently and optionally substituted with 1-4 halo, CN, OR, or $C_{1-6}$alkyl;

each $R^{10}$ is independently selected from $C_{1-6}$ alkyl, halo$C_{1-6}$ alkyl, halo, OR, C(=O)R, $CO_2R$, COCOR, $NO_2$, CN, S(O)R, $SO_2R$, SR, $N(R^4)_2$, $CON(R^4)_2$, $SO_2N(R^4)_2$, OC(=O)R, $N(R^4)COR$, or $N(R^4)CO_2R$;

each $R^4$ is independently selected from H, $C_{1-6}$alkyl, or halo$C_{1-6}$alkyl;

each $R^5$ is independently selected from halo, halo$C_{1-6}$ alkyl, or $C_{1-6}$alkyl; and each R is independently selected from H, $C_{1-6}$alkyl, or halo$C_{1-6}$alkyl;

provided that the compound is not

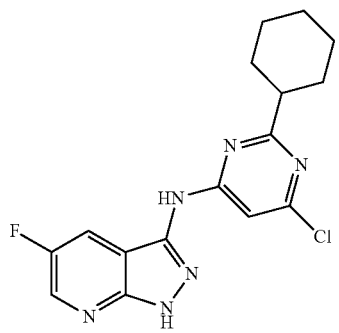

or

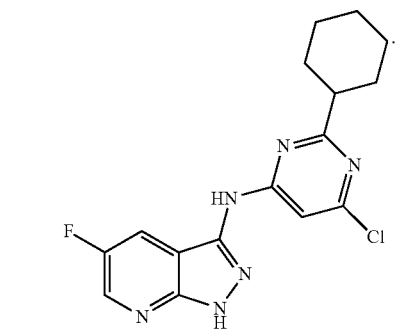

2. The compound according to claim 1 wherein Ht is

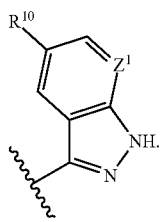

3. The compound according to claim 2, wherein $R^{10}$ is halo.
4. The compound according to claim 3, wherein $R^{10}$ is fluoro.
5. The compound according to claim 3, wherein $Z^1$ is $CR^{10}$.
6. The compound according to claim 4, wherein $Z^1$ is N.
7. The compound according to claim 4, wherein $R^X$ is H or $C_{1-6}$ alkyl, wherein the alkyl is independently and optionally substituted with 1-5 halo.
8. The compound according to claim 7, wherein the alkyl is methyl, ethyl, cyclopropyl, or isopropyl, wherein each alkyl is independently and optionally substituted with 1-5 halo.
9. The compound according to claim 7, wherein $R^X$ is H.
10. The compound according to claim 7, wherein $R^X$ is methyl.
11. The compound according to claim 7, wherein the halo is fluoro.
12. The compound according to claim 7, wherein $R^Y$ is halo or $C_{1-6}$ alkyl.
13. The compound according to claim 12, wherein $R^Y$ is methyl.
14. The compound according to claim 7, wherein $R^Y$ is a 5-6 membered heterocyclyl containing 1-2 heteroatoms selected from O, N, or S.
15. The compound according to claim 14, wherein $R^Y$ is a 6-membered heterocyclyl containing 1-2 heteroatoms selected from O or N.
16. The compound according to claim 15, wherein said heterocyclyl is morpholinyl, piperidinyl, or piperazinyl.
17. The compound according to claim 7, wherein $R^Y$ is H.
18. The compound according to claim 1, wherein Ring D is 5-7 membered cycloaliphatic.
19. The compound according to claim 18, wherein Ring D is cyclopropyl, cyclobutyl, cyclopentyl, cyclohexyl, cycloheptyl, or adamantyl.
20. The compound according to claim 19, wherein Ring D is cyclohexyl.
21. The compound of claim 1 selected from the following:

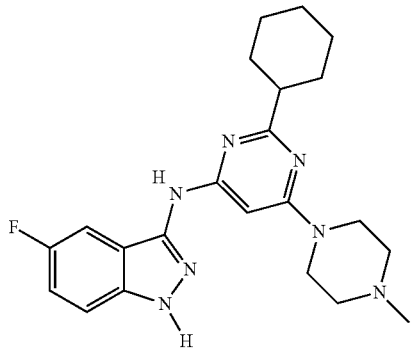

I-2

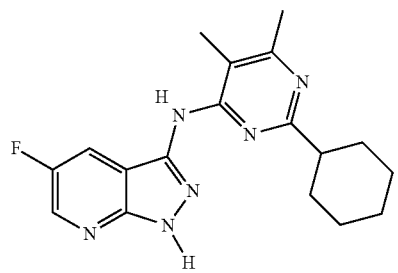

I-3

I-4

I-6

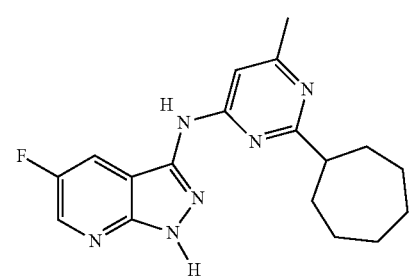

I-7

I-8

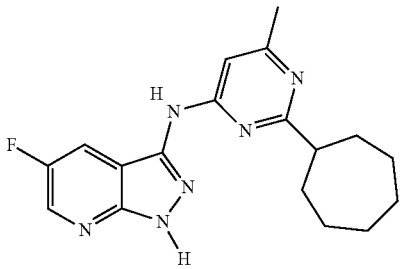

-continued
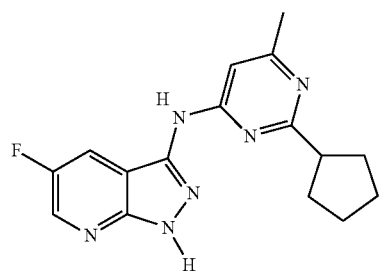
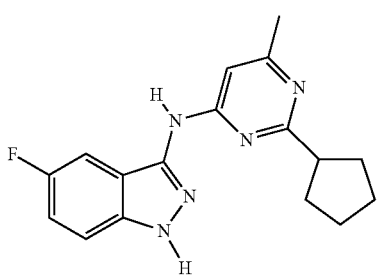

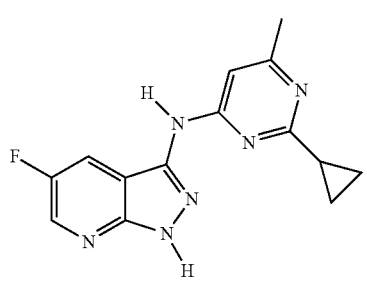
I-20
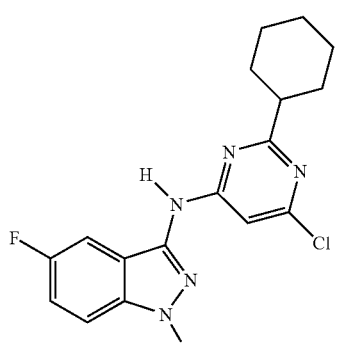
I-22
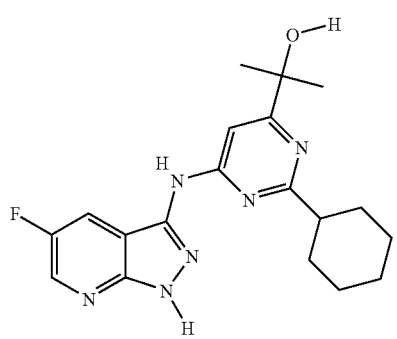
I-21
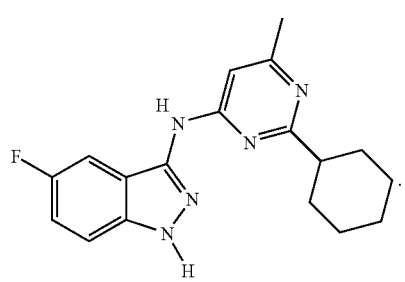
I-23
22. A composition comprising a compound according to claim 1, and a pharmaceutically acceptable carrier, adjuvant, or vehicle.
* * * * *